(12) United States Patent
Vergnolle et al.

US010829563B2

(10) Patent No.: US 10,829,563 B2
(45) Date of Patent: Nov. 10, 2020

(54) METHOD OF SCREENING A CANDIDATE COMPOUND FOR ACTIVITY AS AN ELASTASE 2A (ELA2A) INHIBITOR

(71) Applicants: INSERM (INSTITUT NATIONAL DE LA SANTÉ ET DE LA RECHERCHE MÉDICALE), Paris (FR); Université Toulouse III—Paul Sabatier, Toulouse (FR); CENTRE NATIONAL DE LA RECHERCHE SCIENTIFIQUE (CNRS), Paris (FR)

(72) Inventors: Nathalie Vergnolle, Toulouse (FR); Corinne Rolland, Toulouse (FR); Céline Deraison-Manuel, Toulouse (FR)

(73) Assignees: INSERM (INSTITUTE NATIONAL DE LA SANTÉ ET DE LA RECHERCHE MÉDICALE), Paris (FR); Université Toulouse III—Paul Sabatier, Toulouse (FR); CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 0 days.

(21) Appl. No.: 16/309,280

(22) PCT Filed: Jun. 16, 2017

(86) PCT No.: PCT/EP2017/064786
§ 371 (c)(1),
(2) Date: Dec. 12, 2018

(87) PCT Pub. No.: WO2017/216352
PCT Pub. Date: Dec. 21, 2017

(65) Prior Publication Data
US 2019/0177433 A1    Jun. 13, 2019

(30) Foreign Application Priority Data
Jun. 16, 2016   (EP) .................................... 16305731

(51) Int. Cl.
| | | |
|---|---|---|
| *C12Q 1/37* | (2006.01) |
| *C07K 16/40* | (2006.01) |
| *A61K 38/57* | (2006.01) |
| *C12N 9/00* | (2006.01) |
| *C12N 9/48* | (2006.01) |
| *A61P 1/04* | (2006.01) |
| *C12N 15/113* | (2010.01) |
| *C12N 15/115* | (2010.01) |
| *A61K 39/00* | (2006.01) |

(52) U.S. Cl.
CPC .............. *C07K 16/40* (2013.01); *A61K 38/57* (2013.01); *A61P 1/04* (2018.01); *C12N 9/00* (2013.01); *C12N 9/48* (2013.01); *C12N 15/115* (2013.01); *C12N 15/1137* (2013.01); *C12Q 1/37* (2013.01); *A61K 2039/505* (2013.01); *C07K 2317/76* (2013.01); *C12N 2310/11* (2013.01); *C12N 2310/12* (2013.01); *C12N 2310/14* (2013.01); *C12N 2310/16* (2013.01); *G01N 2333/96433* (2013.01); *G01N 2500/02* (2013.01); *G01N 2500/10* (2013.01); *G01N 2800/065* (2013.01)

(58) Field of Classification Search
CPC ...... C07K 16/40; C07K 2317/76; C12N 9/00; C12N 9/48; C12N 15/1137; C12N 15/115; C12N 2310/11; C12N 2310/12; C12N 2310/14; C12N 2310/16; A61K 2039/505; A61K 38/57; A61P 1/04; C12Q 1/37; G01N 2800/065; G01N 2333/96433; G01N 2500/02; G01N 2500/10

See application file for complete search history.

(56) References Cited

FOREIGN PATENT DOCUMENTS

| | | |
|---|---|---|
| WO | 2006/070012 A1 | 7/2006 |
| WO | 2011/086172 A1 | 7/2011 |
| WO | 2011/107505 A1 | 9/2011 |

OTHER PUBLICATIONS

Szepessy E. and Sahin-Tóth M. (2006) Pancreatology. 6:117-122 (available online at—doi.org/10.1159%2F000090031. Published Dec. 1, 2005).*

(Continued)

*Primary Examiner* — Robert S Landsman
(74) *Attorney, Agent, or Firm* — W&C IP

(57) ABSTRACT

The invention is in the field of therapy of gut inflammatory diseases such as Inflammatory Bowel Diseases (IBD) or Irritable Bowel Syndrome (IBS) including Gluten hypersensitivity. The inventors showed that ELA2A secreted by epithelial cells in the extracellular space is over-expressed in IBD conditions degrading tight junction proteins and controlling cytokines expression. Overexpression of ELA2A conferred a pro-inflammatory phenotype both in cell expression systems and in vivo in animal model of IBD. The inventors also showed that ELA2 over-expressing intestinal epithelial cells increase the release of CXCL8 protein compared to control cells. The increased CXCL-8 protein release observed in cells overexpressing ELA2A is inhibited by ELAFIN addition to the culture, in a dose-dependent manner. In particular, the invention relates to inhibitors of Elastase ELA2A, for use in the treatment of Inflammatory Bowel Diseases, such as Crohn's Disease, Ulcerative Colitis, Celiac disease, and Pouchitis.

8 Claims, 17 Drawing Sheets
Specification includes a Sequence Listing.

(56) References Cited

OTHER PUBLICATIONS

Motta Jean Paul et al: "Food-Grade Lactic Acid Bacteria Expressing Elastase Inhibitors Protect Form Intestinal Inflammation in Acute and Chronic Models of Colitis in Mice", Gastroenterology, vol. 142, No. 5, p. S720, May 2012.

Celine Deraison et al: "Tu1842 Elastolytic Balance in IBD: the Elastase Inhibitor Elafin Prevents Loss of Barrier Function and Cytokines Release by Human Intestinal Epithelial Cells in IBD Conditions", Gastroenterology, vol. 142, No. 5, pp. S-859, May 11, 2012.

Heather J Galipeau et al: "Novel Role of the Serine Protease Inhibitor Elafin in Gluten-Related Disorders", American Journal of Gastroenterology, vol. 109, No. 5, pp. 748-756, May 1, 2014.

Deraison Celine et al: "Elastolytic Baland in IBD: the Elastase Inhibitor Elafin Prevents Loss of Barrier Function and Cytokines Release by Human Intestinal Epithelial Cells in IBD Conditions", Gastroenterology, vol. 142, No. 5, Suppl. 1, p. S859, May 2012.

Chrystelle Bonnart et al: "Elastase 2 is expressed in human and mouse epidermis and impairs skin barrier function in Netherton syndrome through filaggrin and lipid misprocessing", Journal of Clinical Investigarion, American Society for Clinical Investigation, US, vol. 120, No. 3, pp. 871-882, Mar. 1, 2010.

Vergnolle N: "Clinical relevance of proteinase activated receptors (pars) in the gut", GUT, vol. 54, No. 6, pp. 867-874, 2005.

Vergnolle N et al: "Protease-activated receptors in inflammation, neuronal signaling and pain", Trends in Pharcological Sciences, vol. 22, No. 3, pp. 146-152, 2001.

Vergnolle N et al: "Proteinase-activated receptors: novel signals for peripheral nerves", Trends in Neurosciences, vol. 26, No. 9, pp. 496-500, 2003.

Isabelle Cleynen et al: "Genetic Evidence Supporting the Association of Protease and Protease Inhibitor Genes with Inflammatory Bowel Disease: A Systematic Review", PLOS One, vol. 6, No. 9, p. e24106, Sep. 8, 2011.

Pham CT: "Neutrophil serine proteases: specific regulators of inflammation", Nature Reviews Immunology, vol. 6, No. 7, pp. 541-550, 2006.

* cited by examiner

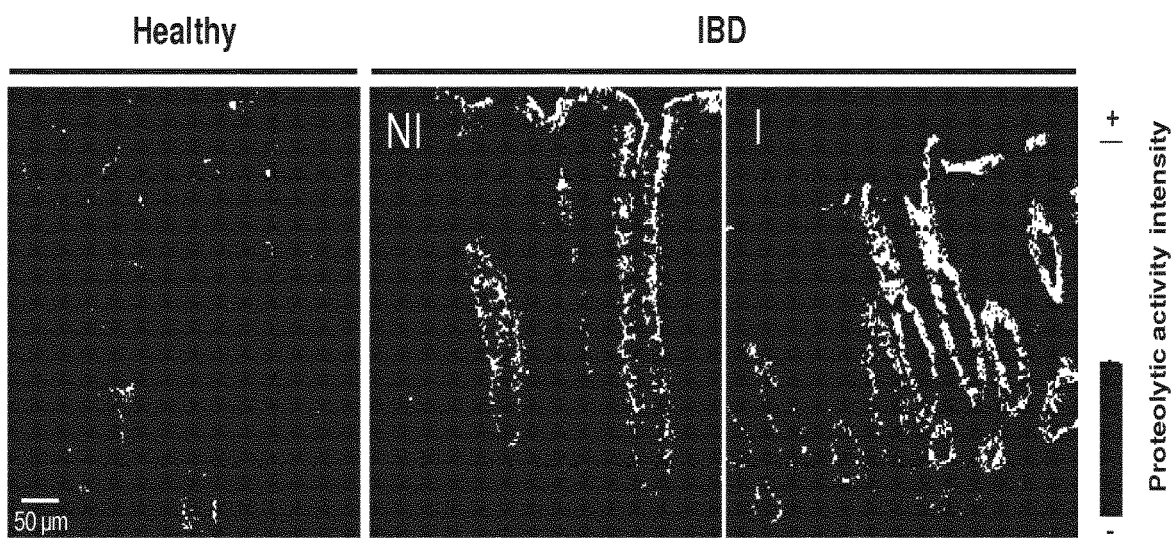
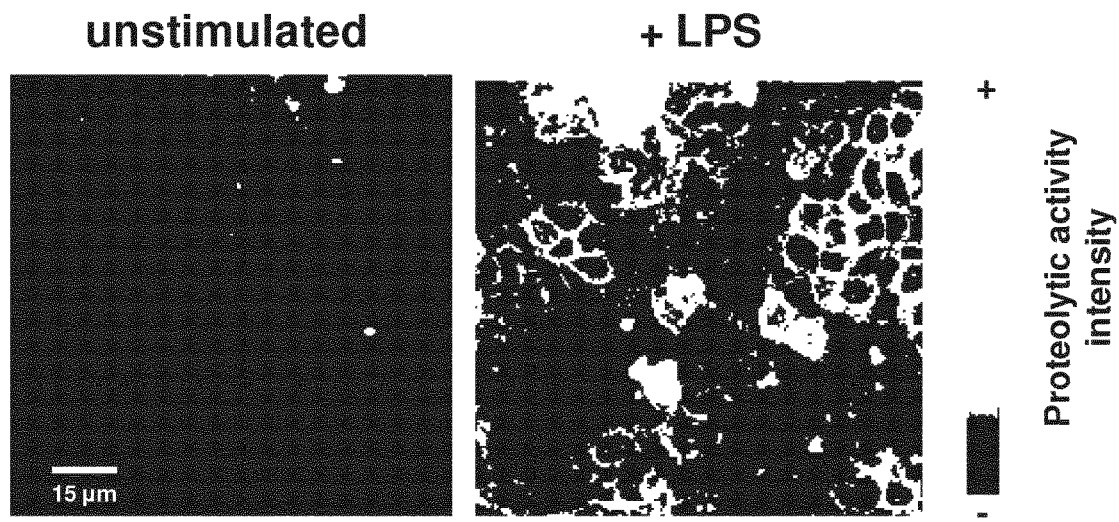
Figure 1 A and B

Figure 2:
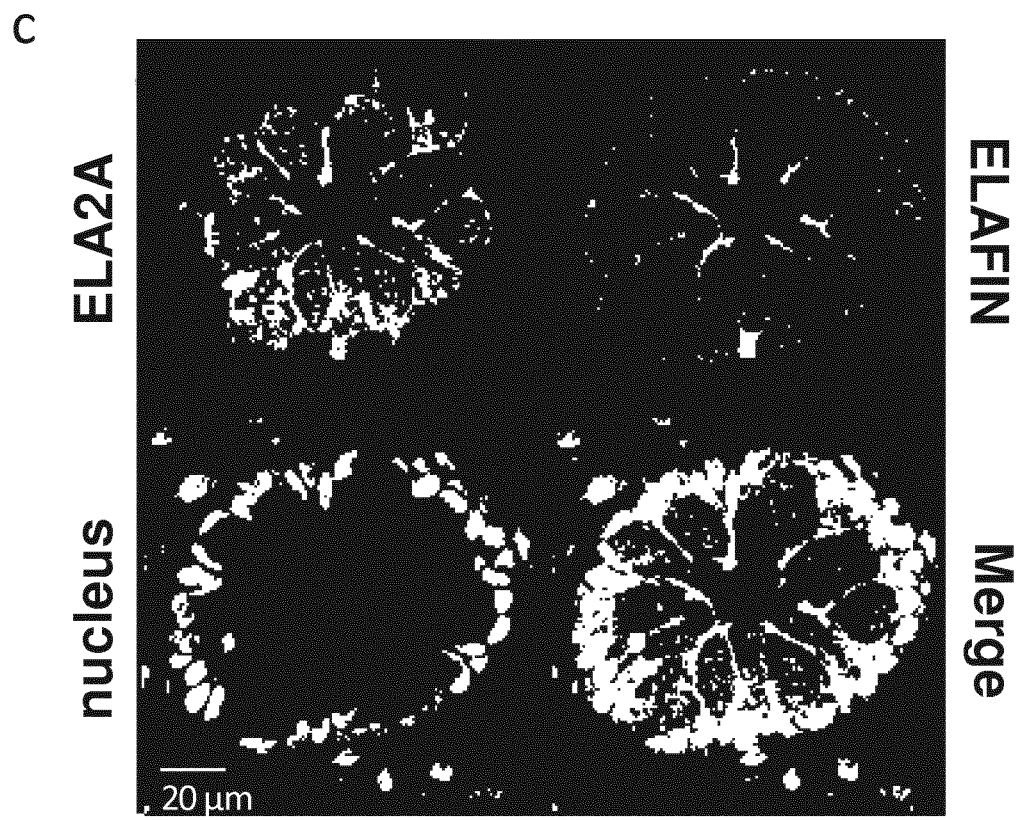

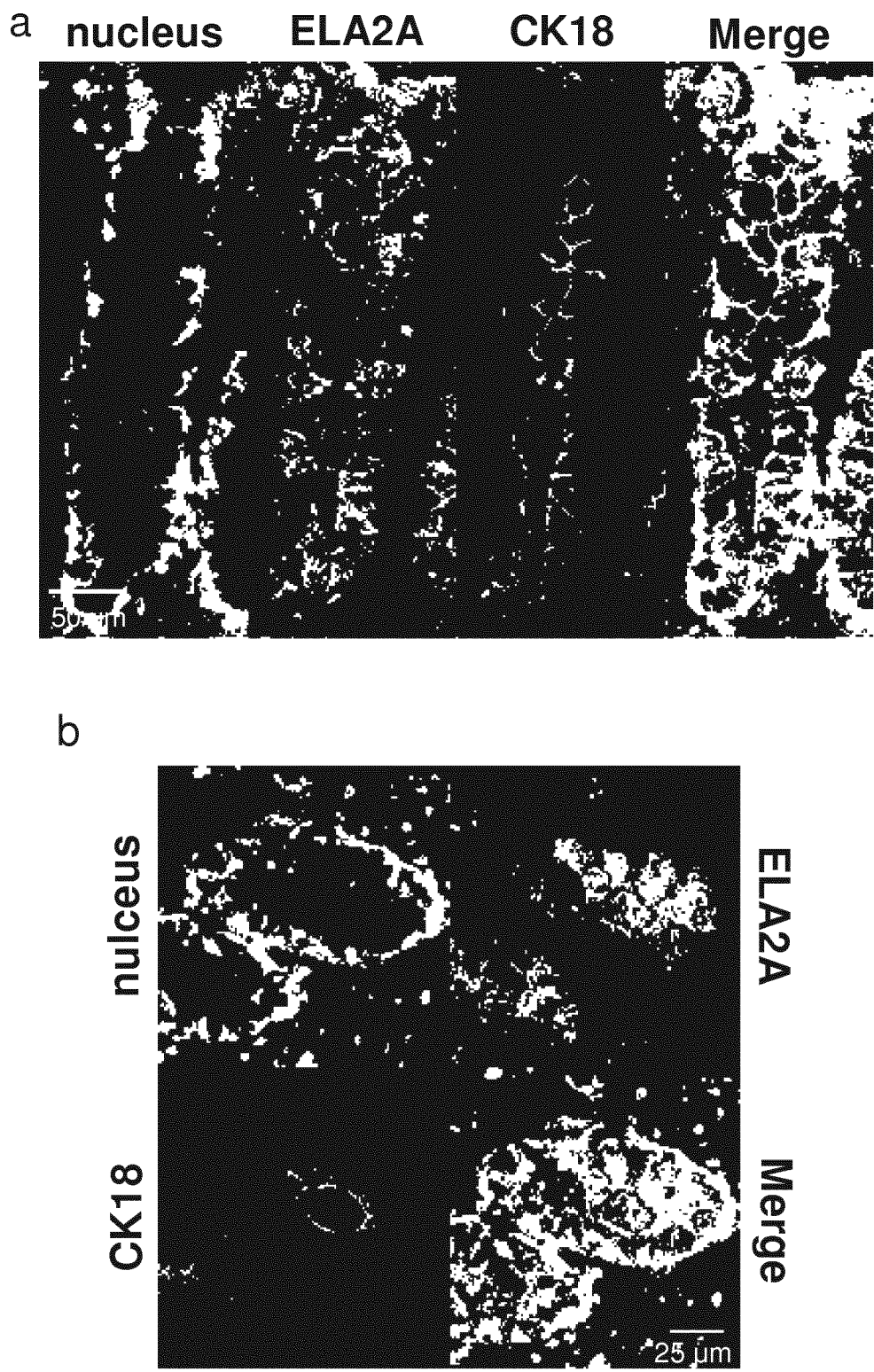
Figure 2 A and B

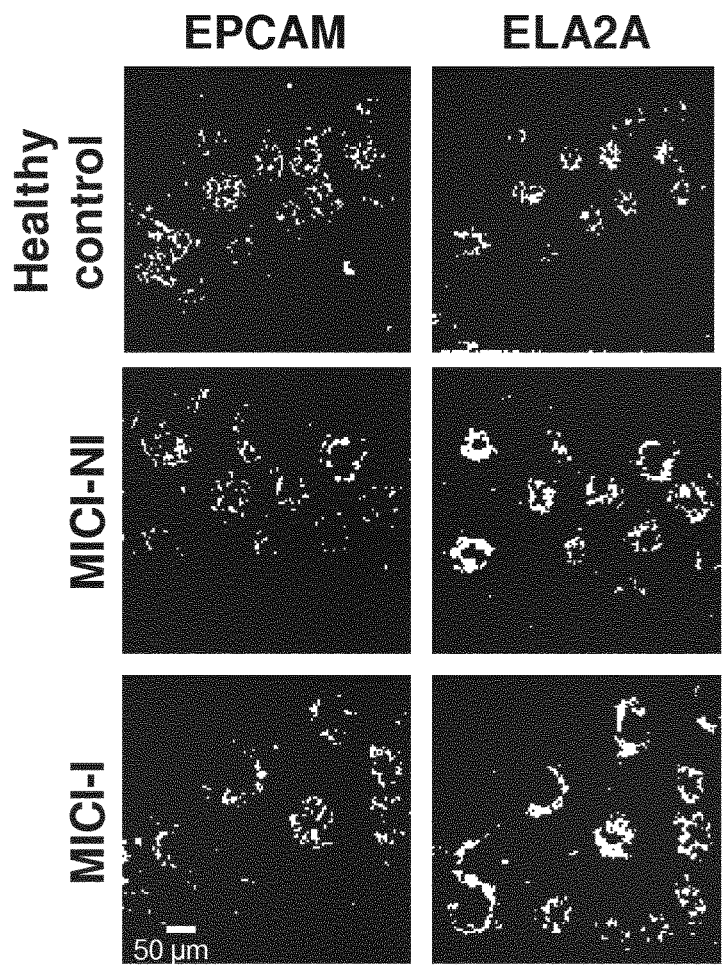
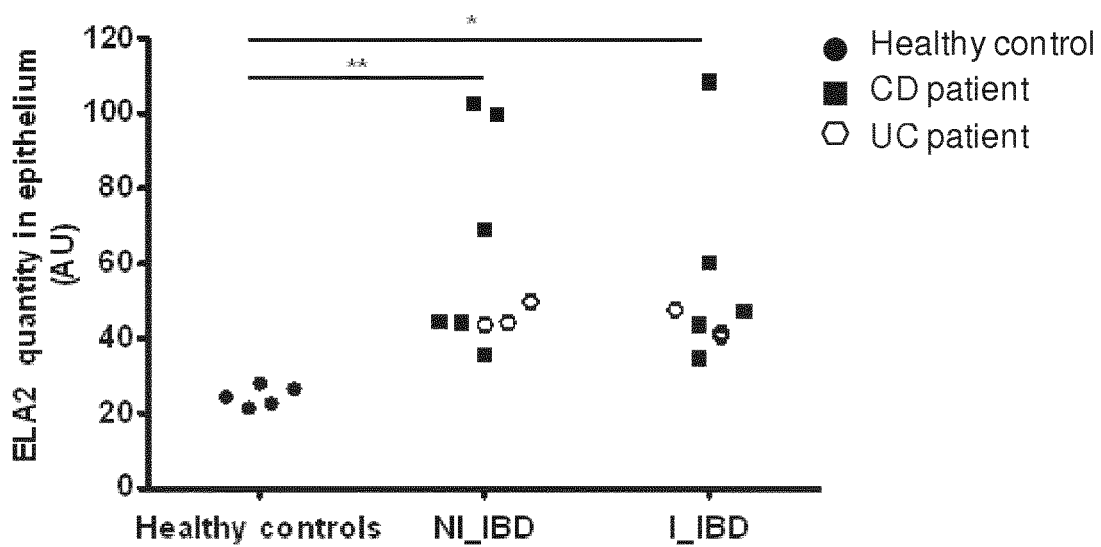
Figure 3 A and B

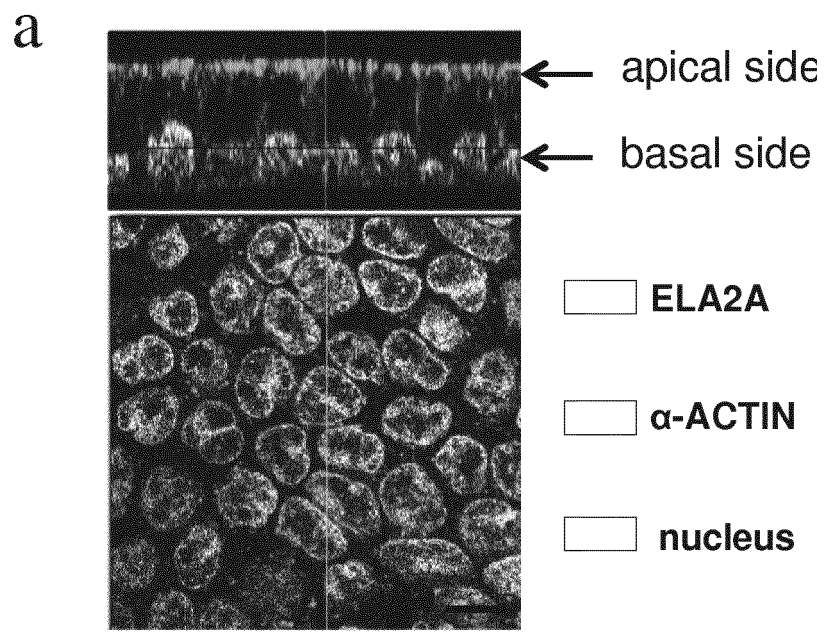
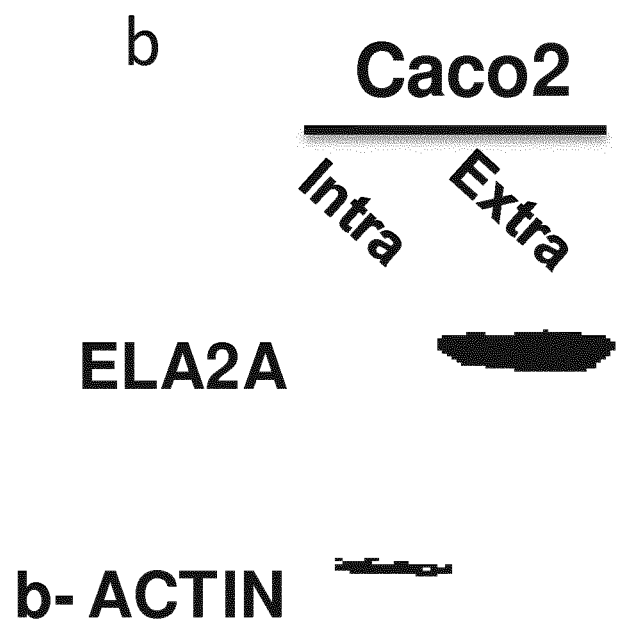
Figure 4 A and B

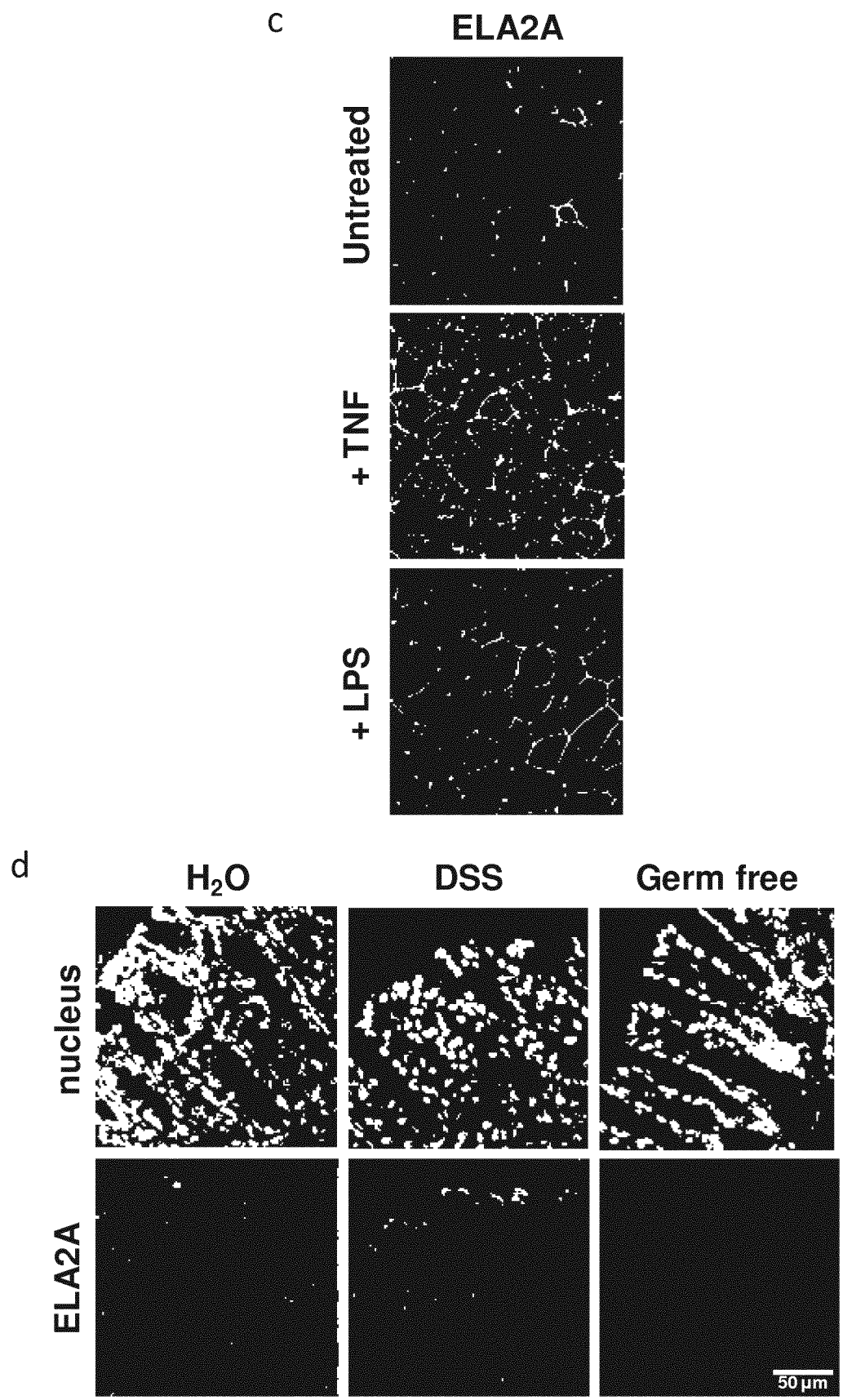
Figure 4 C and D

Figure 5:
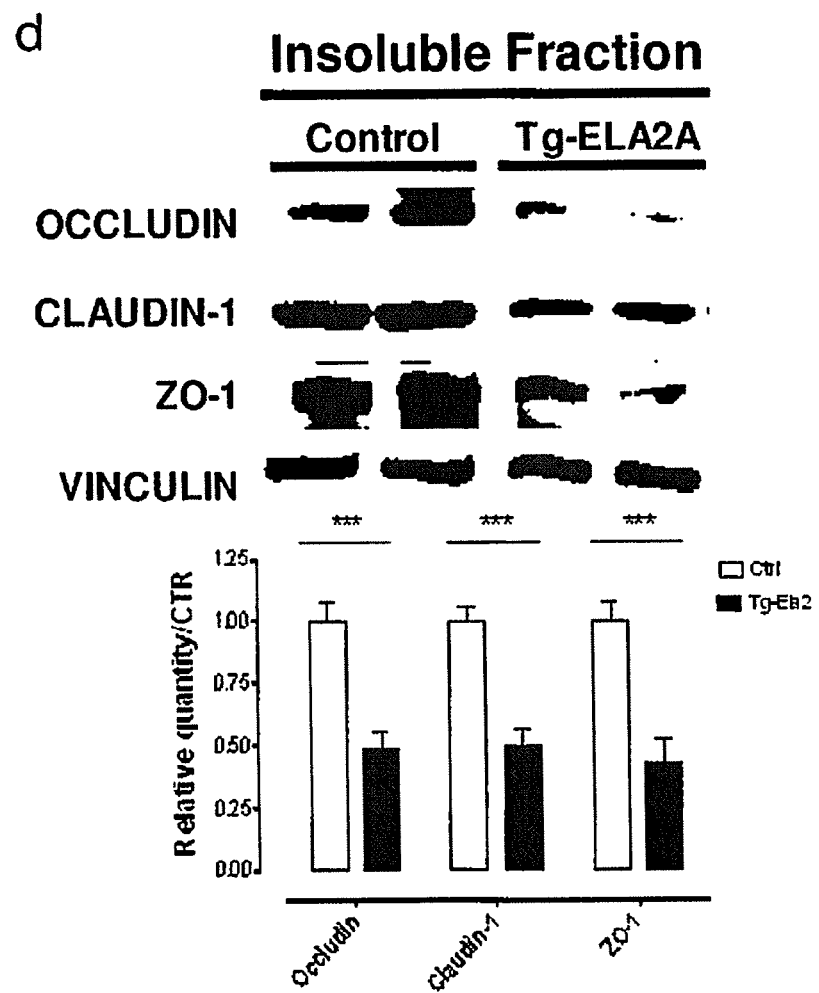
Figure 5:
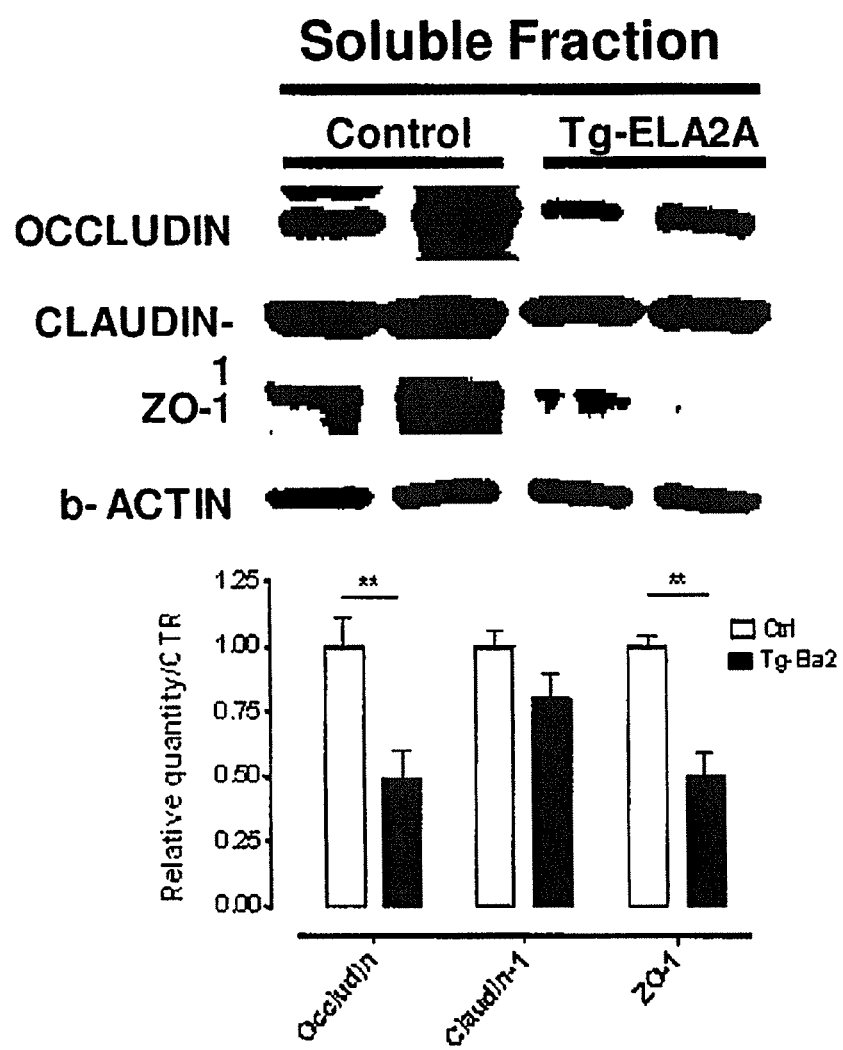
Figure 5:
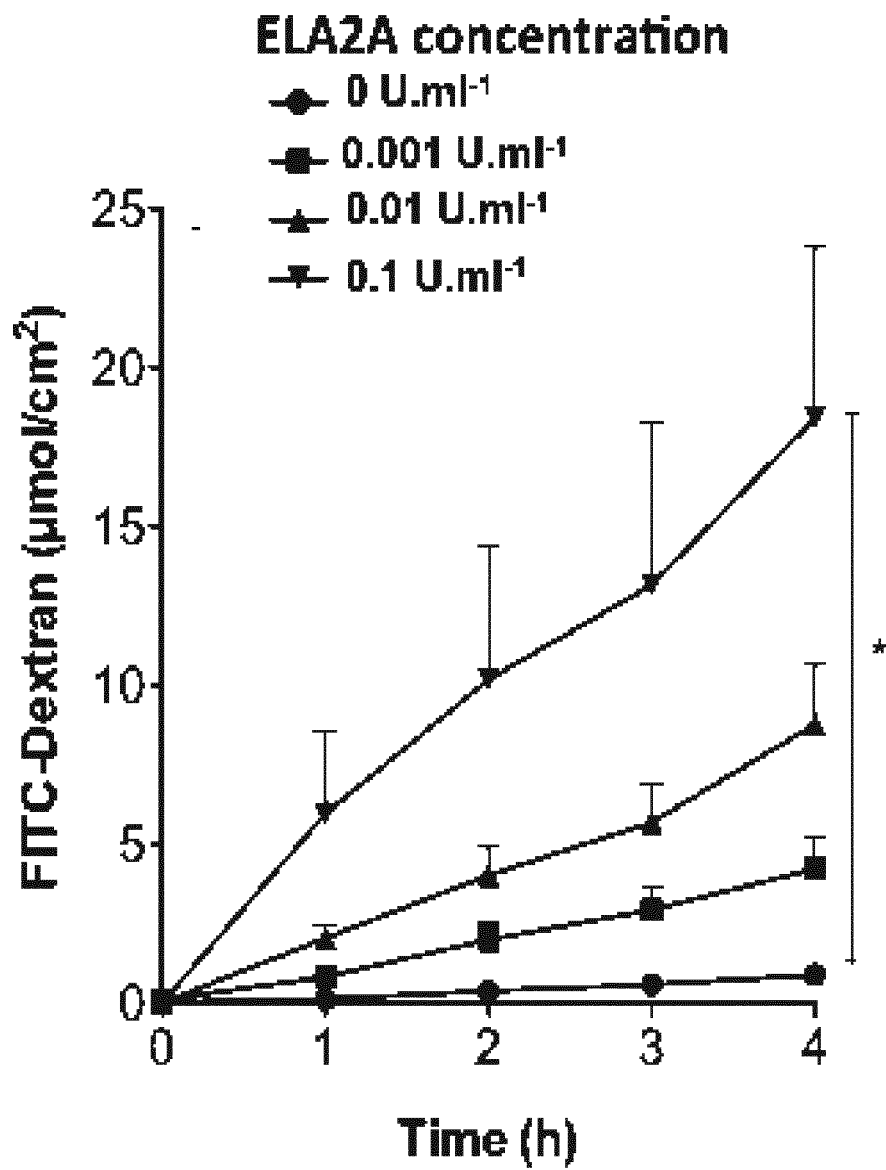

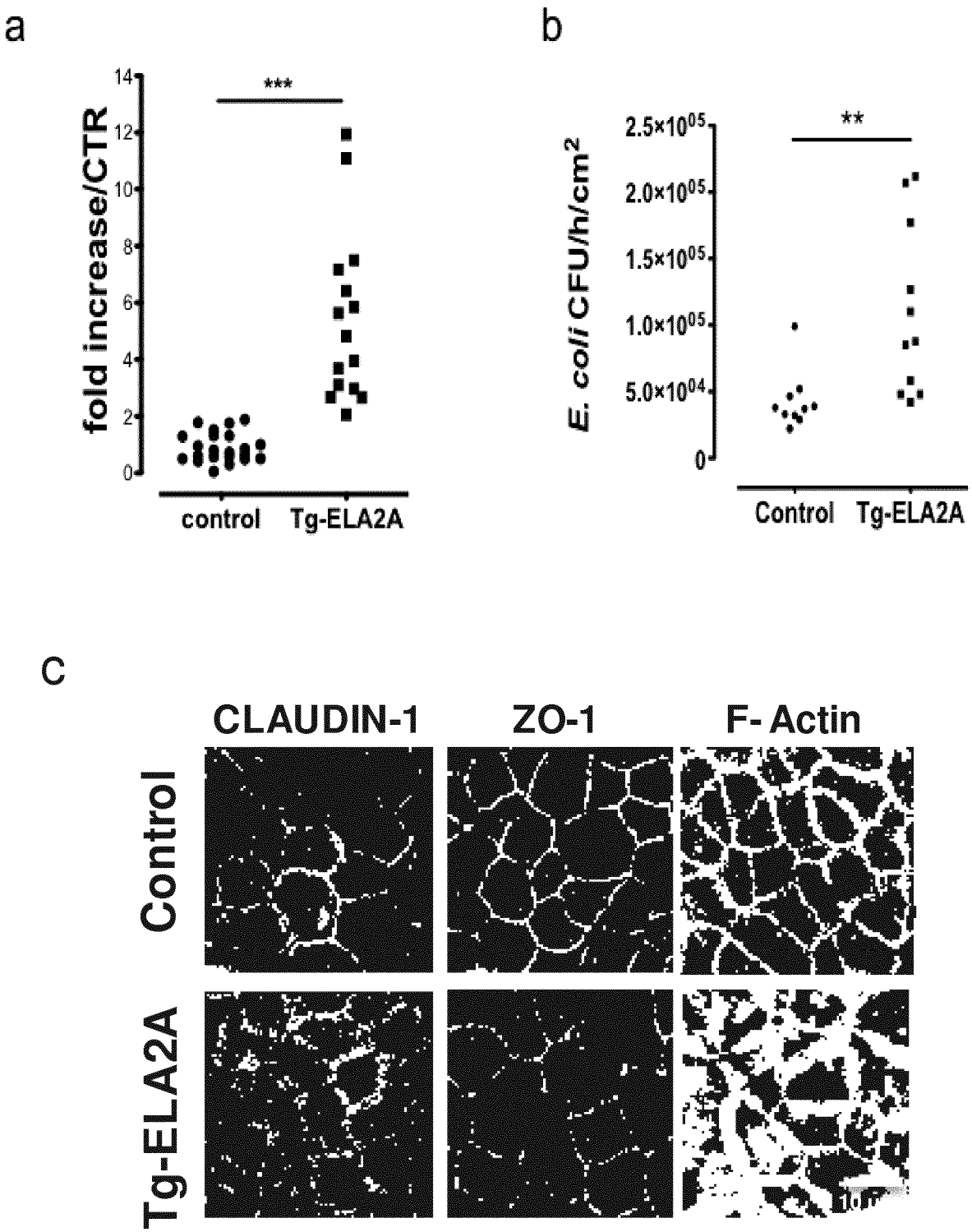
Figure 5 A, B and C

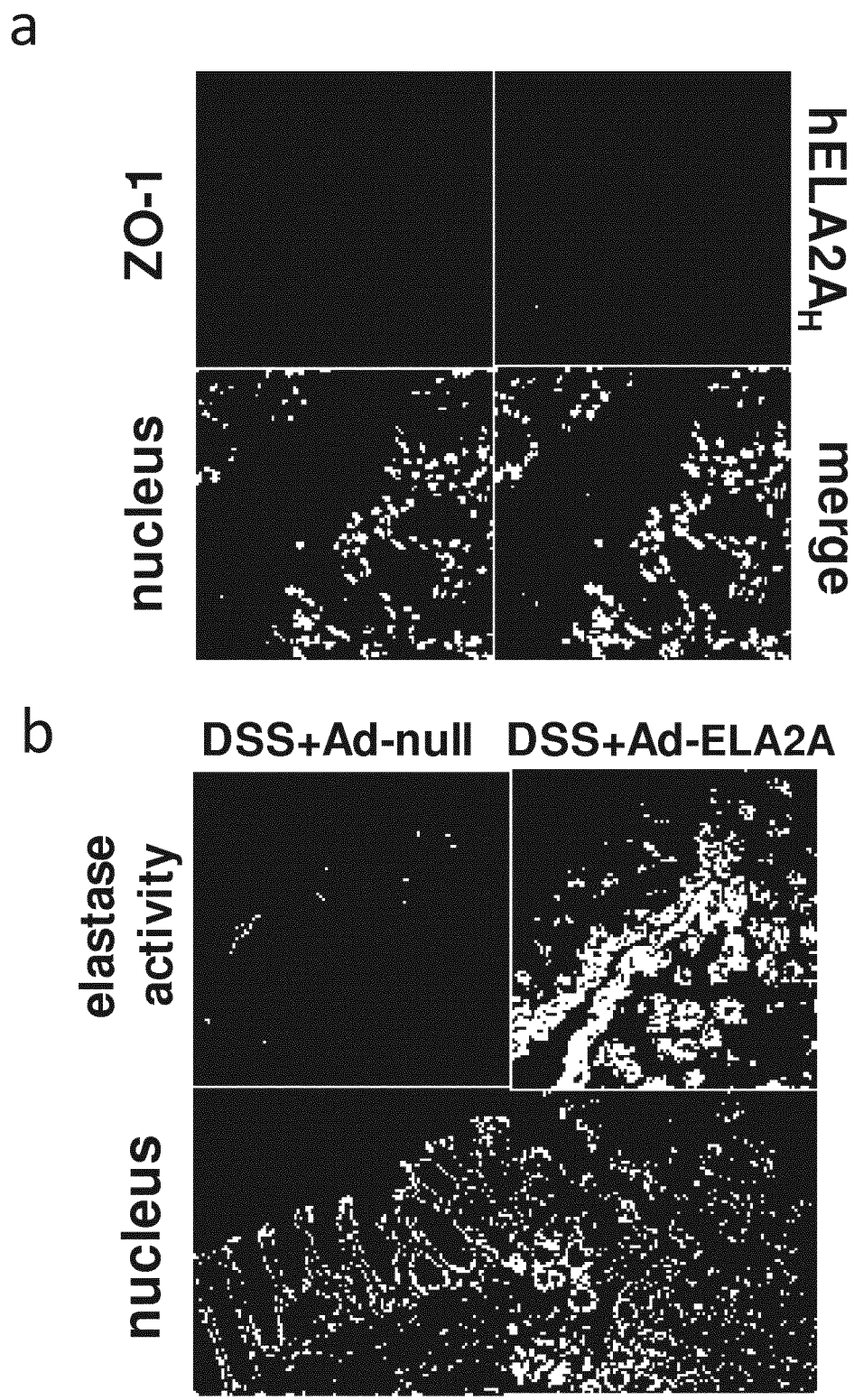
Figure 7A and B

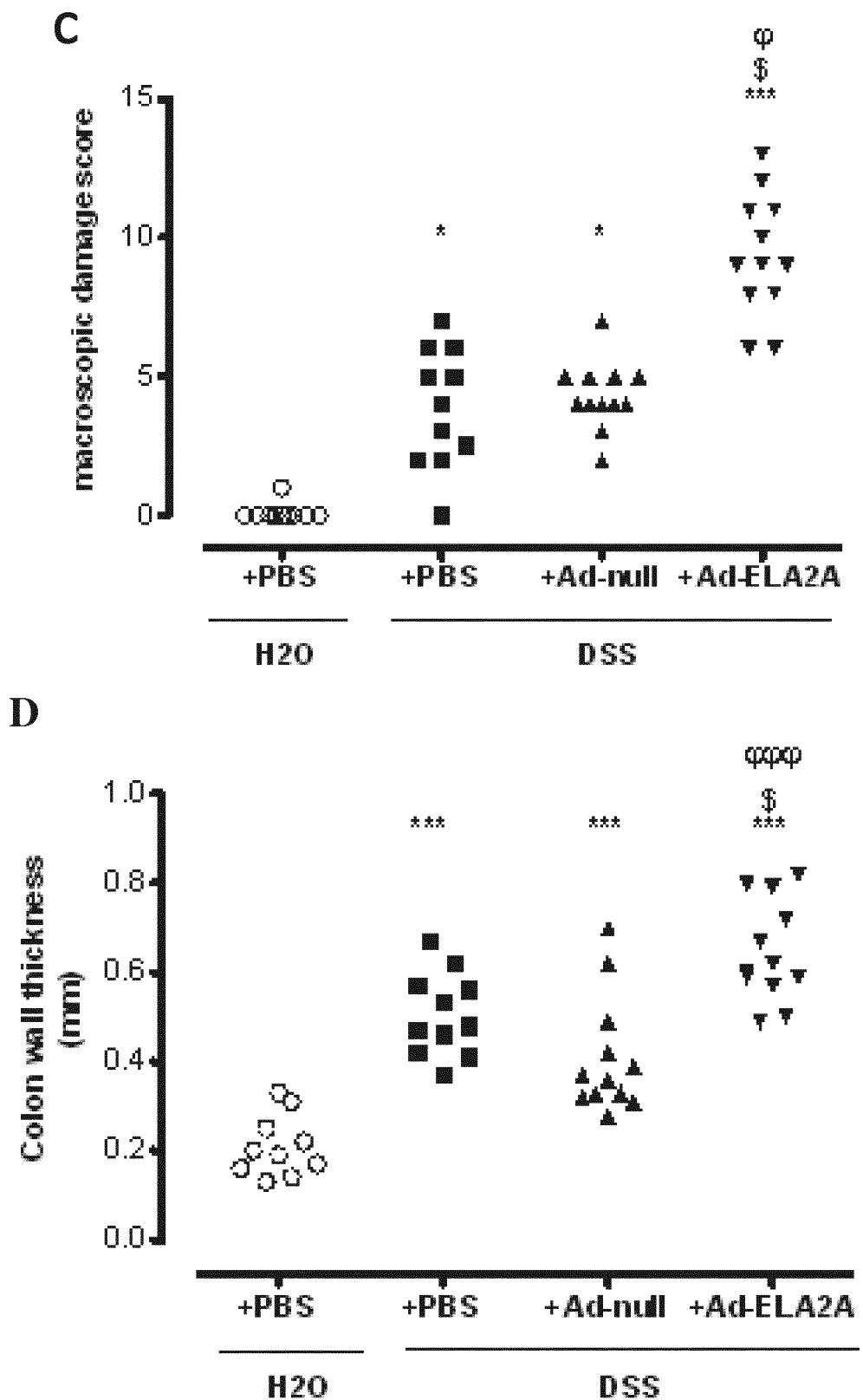
Figure 7 C and D

E
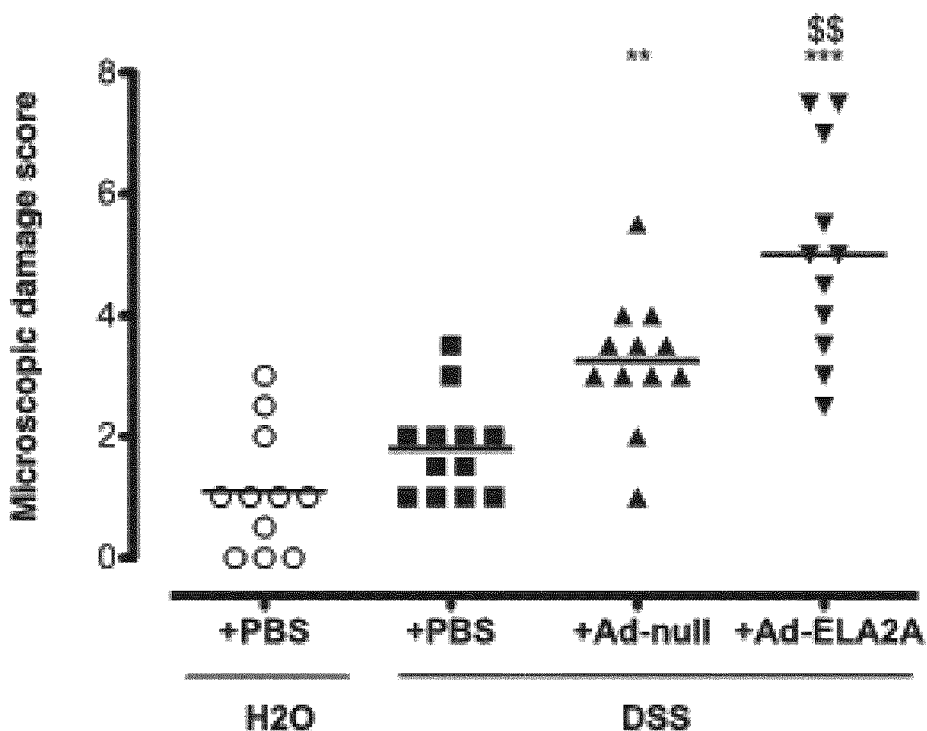
f
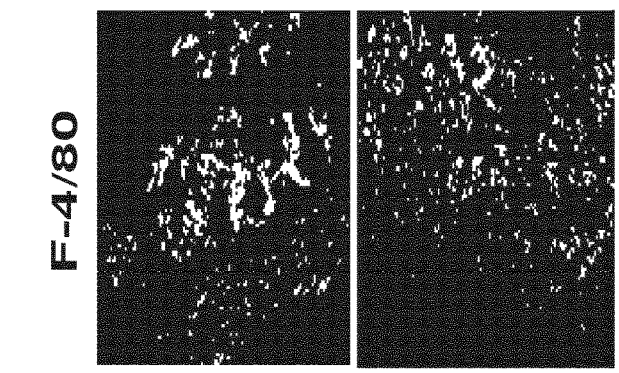
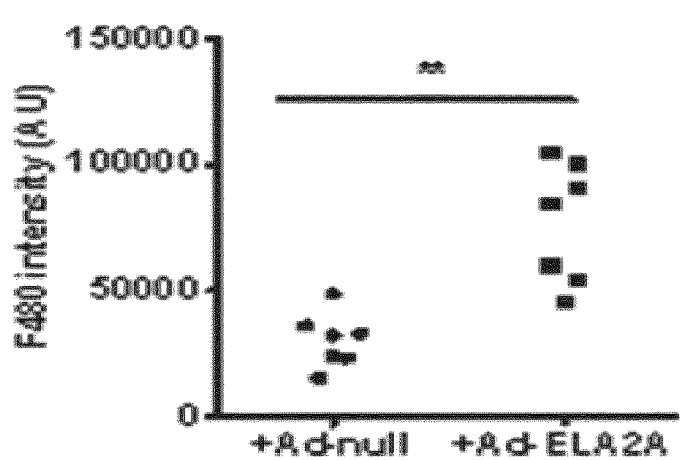
Figure 7 E and F

SEQUENCE LISTING

```
<160> NUMBER OF SEQ ID NOS: 3

<210> SEQ ID NO 1
<211> LENGTH: 21
<212> TYPE: RNA
<213> ORGANISM: Artificial
<220> FEATURE:
<223> OTHER INFORMATION: Synthetic Antisens 1 ELA2A : start at 55 on CDS

<400> SEQUENCE: 1
auaagguggg uaaguggggu c                                             21

<210> SEQ ID NO 2
<211> LENGTH: 21
<212> TYPE: RNA
<213> ORGANISM: Artificial
<220> FEATURE:
<223> OTHER INFORMATION: Synthetic Antisens 2 ELA2A : start at 291 on
      CDS

<400> SEQUENCE: 2
uuagagacac ugacugccag c                                             21

<210> SEQ ID NO 3
<211> LENGTH: 21
<212> TYPE: RNA
<213> ORGANISM: Artificial
<220> FEATURE:
<223> OTHER INFORMATION: Synthetic Antisens 3 ELA2A : start at 437 on
      CDS

<400> SEQUENCE: 3
aguuguuggg uagaauggug c                                             21
```

METHOD OF SCREENING A CANDIDATE COMPOUND FOR ACTIVITY AS AN ELASTASE 2A (ELA2A) INHIBITOR

FIELD OF THE INVENTION

The invention is in the field of therapy of gut inflammatory diseases such as Inflammatory Bowel Diseases (IBD), Irritable Bowel Syndrome (IBS), celiac disease or pouchitis. In particular, the invention relates to inhibitors of Elastase Ela2A, for use in the treatment of Irritable Bowel Syndrome (IBS) including gluten hypersensitivity, of Inflammatory Bowel Diseases such as Crohn's Disease and Ulcerative Colitis or for Celiac disease and Pouchitis.

BACKGROUND OF THE INVENTION

Proteinases (usually termed "proteases) act as both positive and negative effectors of several biological processes either broadly as catalysts of protein degradation or specifically as selective agents that control physiological processes. Proteases can send specific signals to cells, either through the generation of active mediators being activated upon cleavage of their precursor form, or through the activation of receptors, such as the Protease-Activated Receptors (PARs) (1). Proteases are major proteins in inflammatory cells. They are released massively by damaged cells and are also often released by microorganisms, thereby contributing to their pathogenicity. As such, different serine proteases are now considered as active players of chronic inflammatory diseases (2-5). Proteases released by infiltrating leukocytes during gut inflammation play a key role in determining mucosal lesions through the digestion of the extracellular matrix and the alteration of the epithelial barrier function (6). Additionally, neutrophil elastase, proteinase-3, or trypsin, are known to exert pro-inflammatory effects in mucosal tissues, leading to the release of pro-inflammatory cytokines, chemokines and other inflammatory mediators (5, 7, 8). Which of those proteases are playing a detrimental role in chronic inflammatory disorders, and may be considered as potential therapeutic targets is still an open question. The present invention falls within this context of defining the proteases that are playing a significant role in inflammatory bowel diseases (IBD).

IBD, including Crohn's disease and ulcerative colitis, are characterized by chronic relapsing intestinal inflammation. It has been a worldwide health-care problem with a continually increasing incidence (9). Although the aetiology of IBD remains largely unknown, it involves a complex interaction between the genetic, environmental or microbial factors and the immune responses (10). Recent studies have demonstrated that elastase activity is significantly increased both in animal models of colitis and in patients suffering from IBD (5, 8, 11, 12). Interestingly, elastase activity is largely released by mucosal tissues from IBD patients, even at sites distant from the inflammation (tissues with no inflammatory signs) (5). Specific inhibition of elastase activity by the protease inhibitor ELAFIN has protective effects in rodent models of chronic inflammatory disorders of the gut (5, 8). Taken together, those findings support the concept that elastolytic balance (protease/anti-protease activities) in IBD is broken and that proteases from the elastase family take-on a key role in the pathogenesis of intestinal inflammation. The original aim of this study was to define the elastolytic proteases that are present in tissues from IBD patients.

Although it can be hypothesized that a large amount of elastolytic activity associated with inflammation could come from infiltrating neutrophils, it cannot rule out that elastolytic activity could come also from other sources (bacteria, resident cells), and might bear forms of elastase other than neutrophil elastase. This last hypothesis could be particularly true in non-inflamed tissues from IBD patients, which presented increased elastolytic activity in absence of granulocyte infiltration. To this end inventors used in situ zymography and biochemical approach to localyse elastolytic activity in colon samples from individuals with IBD and in cultures of colon-derived cultured epithelial cells. Their data reveal that in intestine epithelial cells are a major source of elastase activity. They then identified ELASTASE 2A (ELA2A) as the predominant protease expressed and secreted by epithelial cells and deciphered its implication in pathophysiological pathways of IBD.

Based on this knowledge, the inventors propose identification of a new protease associated with inflammation into the gut of IBD patient, which could be used as a new target for the treatment of IBD or IBS.

SUMMARY OF THE INVENTION

The invention is based on the discovery that the ELASTASE 2A (ELA2A) is implicated in pathophysiological pathways of IBD. Indeed, inventors shown that in gut epithelium from IBD patients, ELA2A expression was enhanced. ELA2A secreted by epithelial cells in the extracellular space is over-expressed in IBD conditions degrading tight junction proteins and controlling cytokines expression. Overexpression of ELA2A conferred a pro-inflammatory phenotype both in cell expression systems and in vivo in animal model of IBD. ELA2A thus appears as a newly discovered epithelial protease involved in the pathogenesis of IBD through essential pathways for colonic barrier function. So the present inventors discovered ELA2A as a new potential target for gut inflammatory diseases treatment or Irritable Bowel Syndrome (IBS) treatment.

Thus, the invention relates to an inhibitor of ELA2A for the treatment of gut inflammatory diseases or Inflammatory Bowel Diseases (IBD), such as Crohn's Disease, Ulcerative Colitis, Celiac disease, and pouchitis. The invention also relates to an inhibitor of ELA2A for the treatment of Irritable Bowel Syndrome (IBS) and gluten hypersensitivity.

A further object of the invention relates to a therapeutic composition comprising inhibitor of ELA2A as defined above.

DETAILED DESCRIPTION OF THE INVENTION

As previously mentioned the inventors demonstrate that in IBD conditions, ELA2 is over-expressed in epithelial cells and that hyperactive ELA2A participates to principal determinants of IBD pathogenesis: (i) increase permeability of intestinal epithelial barrier which leads to penetration of luminal products into the mucosa and (ii) induce abnormal immune status of epithelial cells leading to innate immune cells infiltration and cytokine driven inflammation.

ELA2A Inhibitor

Reducing the elastolytic activity associated with inflammation is known improve prognosis among patients gut inflammatory diseases such as Inflammatory Bowel Diseases (IBD) (Motta, J. P et al Gastroenterology 2011, Motta, J. P et al Science Trans. Med. 2012 and Bermudez-Humaran, L et al, Microbial Cell Factories, 2015). Accordingly use of ELA2A inhibitor (inhibitor of expression or of activity) may be used to treat gut inflammatory diseases such as Inflammatory Bowel Diseases (IBD).

Accordingly ELA2A inhibitor (inhibitor of expression or of activity) may be used to treat Inflammatory Bowel Diseases (IBD) or Irritable Bowel Syndrome (IBS).

In particular embodiment Inflammatory Bowel Diseases (IBD), is selected between the group of Crohn's Disease, Ulcerative Colitis Celiac disease, Gluten hypersensitivity and Pouchitis.

Accordingly the present invention, a functional assays may be envisaged to determined an ELA2A inhibitor, such inhibition of elastatic activity, like Elastolytic activity assay (see Example and FIG. 1) which could be also used to evaluate the ability of ELA2A inhibitors to block specific gut inflammation condition (see Example and FIG. 5, FIG. 6 and Motta et al Gastroenterology 2011):

The functional assay may be also an elastase inhibitor functional assay: Recombinant ELA2A is incubated with qFITC-elastin and a time course dependent assay is performed to quantify fluorescence released after elastin cleavage by ELA2A. Presence of ELA2A inhibitor in the reaction milieu will decrease the fluorescence quantity du to decrease of ELA2A activity. (Bonnart et al. JCI 2010)

Accordingly a first object of the present invention is an ELA2A inhibitor for use in treating of Inflammatory Bowel Diseases (IBD) or Irritable Bowel Syndrome (IBS) in a patient.

As used herein, the term "inflammatory bowel diseases (IBD)" is a group of inflammatory diseases of the colon and small intestine. The major types of IBD are Crohn's disease, ulcerative colitis Celiac disease, and pouchitis.

As used herein, the term "Irritable Bowel Syndrome (IBS)" is a term for a variety of pathological conditions causing discomfort in the gastro-intestinal tract. It is a functional bowel disorder characterized by chronic abdominal pain, discomfort, bloating, and alteration of bowel habits in the absence of any organic cause. It also includes some forms of food-related visceral hypersensitivity, such as Gluten hypersensitivity.

The term "ELA2A" also known as "ELASTASE 2A" or "chymotrypsin-like elastase family, member 2A" means Elastase 2A (NM_033440→NP_ NP_254275 NM/(EC 3.4.21.71)) which is a elastase enzyme that in humans is encoded by the CELA2A gene. Elastases form a subfamily of serine proteases that hydrolyze many proteins in addition to elastin. Humans have six elastase genes which encode the structurally similar proteins elastase 1, 2, 2A, 2B, 3A, and 3B. Like most of the human elastases, elastase 2A is secreted from the pancreas as a zymogen. In other species, elastase 2A has been shown to preferentially cleave proteins after leucine, methionine, and phenylalanine residues. Clinical literature that describes human elastase 1 activity in the pancreas is actually referring to elastase 2A. ELA2A expression has been well described in skin, more precisely in the granular layer of epithelium (Bonnart 2010, JCI). The whole sequence of human Ela2A gene (gene CELA2A) is referenced as Gene ID: 63036

Inhibitors of the ELA2A Expression

A further object of the present invention relates to an ELA2A inhibitor, which is an inhibitor of the ELA2A expression for use in the treatment of Inflammatory Bowel Diseases (IBD) or Irritable Bowel Syndrome (IBS), including Gluten hypersensitivity.

In particular embodiment Inflammatory Bowel Diseases (IBD), is selected between the group of Crohn's Disease, Ulcerative Colitis, Celiac disease, and Pouchitis.

Small inhibitory RNAs (siRNAs) can also function as inhibitors of ELA2A gene expression for use in the present invention. ELA2A gene expression can be reduced by contacting a subject or cell with a small double stranded RNA (dsRNA), or a vector or construct causing the production of a small double stranded RNA, such that ELA2A gene expression is specifically inhibited (i.e. RNA interference or RNAi). Methods for selecting an appropriate dsRNA or dsRNA-encoding vector are well known in the art for genes whose sequence is known (e.g. see for example Tuschl, T. et al. (1999); Elbashir, S. M. et al. (2001); Hannon, G J. (2002); McManus, M T. et al. (2002); Brummelkamp, T R. et al. (2002); U.S. Pat. Nos. 6,573,099 and 6,506,559; and International Patent Publication Nos. WO 01/36646, WO 99/32619, and WO 01/68836).

Examples of oligonucleotide antisense targeting ELA2A gene are:

```
                                            SEQ ID NO: 1
5'-AUAAGGUGGGUAAGUGGGGUC-3' (start at 55 on CDS):

SEQ ID NO: 2
5'-UUAGAGACACUGACUGCCAGC-3' (start at 291 on CDS):

SEQ ID NO: 3
5'-AGUUGUUGGGUAGAAUGGUGC-3' (start at 437 on CDS):
```

Ribozymes can also function as inhibitors of ELA2A gene expression for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of ELA2A mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable. The suitability of candidate targets can also be evaluated by testing their accessibility to hybridization with complementary oligonucleotides, using, e.g., ribonuclease protection assays.

Both antisense oligonucleotides and ribozymes useful as inhibitors of ELA2A gene expression can be prepared by known methods. These include techniques for chemical synthesis such as, e.g., by solid phase phosphoramadite chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

Antisense oligonucleotides siRNAs and ribozymes of the invention may be delivered in vivo alone or in association with a vector. In its broadest sense, a "vector" is any vehicle capable of facilitating the transfer of the antisense oligonucleotide siRNA or ribozyme nucleic acid to the cells and preferably cells expressing ELA2A. Preferably, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the antisense oligonucleotide siRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rouse sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

Preferred viral vectors are based on non-cytopathic eukaryotic viruses in which non-essential genes have been replaced with the gene of interest. Non-cytopathic viruses include retroviruses (e.g., lentivirus), the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, 1990 and in Murry, 1991.

Preferred viruses for certain applications are the adenoviruses and adeno-associated viruses, which are double-stranded DNA viruses that have already been approved for human use in gene therapy. The adeno-associated virus can be engineered to be replication deficient and is capable of infecting a wide range of cell types and species. It further has advantages such as, heat and lipid solvent stability; high transduction frequencies in cells of diverse lineages, including hemopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well known to those of skill in the art. See e.g. Sambrook et al., 1989. In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pBR322, pUC18, pUC19, pRC/CMV, SV40, and pBlueScript. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intramuscular, eye, intradermal, subcutaneous, or other routes. It may also be administered by intranasal sprays or drops, rectal suppository and orally. It may also be administered into the epidermis or a mucosal surface using a gene-gun. The plasmids may be given in an aqueous solution, dried onto gold particles or in association with another DNA delivery system including but not limited to liposomes, dendrimers, cochleate and microencapsulation.

In a preferred embodiment, the antisense oligonucleotide, siRNA, shRNA or ribozyme nucleic acid sequence is under the control of a heterologous regulatory region, e.g., a heterologous promoter.

Inhibitors of the ELA2A Activity

A further aspect of the present invention relates to an ELA2A inhibitor which is an inhibitor of the ELA2A activity for use in the treatment of Inflammatory Bowel Diseases (IBD) or Irritable Bowel Syndrome (IBS) including Gluten hypersensitivity.

In particular embodiment Inflammatory Bowel Diseases (IBD), is selected between the group of Crohn's Disease, Ulcerative Colitis, Celiac disease, and Pouchitis.

In a particular embodiment, the present invention relates to compound which is an inhibitor of the ELA2A activity for use in the treatment of Inflammatory Bowel Diseases (IBD), wherein said compound is an anti-ELA2A antibody which neutralizes ELA2A or an anti-ELA2A antibody fragment which neutralizes ELA2A.

Antibodies directed against ELA2A can be raised according to known methods by administering the appropriate antigen or epitope to a host animal selected, e.g., from pigs, cows, horses, rabbits, goats, sheep, and mice, among others. Various adjuvants known in the art can be used to enhance antibody production. Although antibodies useful in practicing the invention can be polyclonal, monoclonal antibodies are preferred. Monoclonal antibodies against ELA2A can be prepared and isolated using any technique that provides for the production of antibody molecules by continuous cell lines in culture. Techniques for production and isolation include but are not limited to the hybridoma technique originally described by Kohler and Milstein (1975); the human B-cell hybridoma technique (Cote et al., 1983); and the EBV-hybridoma technique (Cole et al. 1985). Alternatively, techniques described for the production of single chain antibodies (see e.g., U.S. Pat. No. 4,946,778) can be adapted to produce anti-ELA2A single chain antibodies. ELA2A activity inhibitors useful in practicing the present invention also include anti-ELA2A antibody fragments including but not limited to F(ab')2 fragments, which can be generated by pepsin digestion of an intact antibody molecule, and Fab fragments, which can be generated by reducing the disulfide bridges of the F(ab')2 fragments. Alternatively, Fab and/or scFv expression libraries can be constructed to allow rapid identification of fragments having the desired specificity to ELA2A.

Humanized anti-ELA2A antibodies and antibody fragments therefrom can also be prepared according to known techniques. "Humanized antibodies" are forms of non-human (e.g., rodent) chimeric antibodies that contain minimal sequence derived from non-human immunoglobulin. For the most part, humanized antibodies are human immunoglobulins (recipient antibody) in which residues from a hypervariable region (CDRs) of the recipient are replaced by residues from a hypervariable region of a non-human species (donor antibody) such as mouse, rat, rabbit or nonhuman primate having the desired specificity, affinity and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. Methods for making humanized antibodies are described, for example, by Winter (U.S. Pat. No. 5,225,539) and Boss (Celltech, U.S. Pat. No. 4,816,397).

Then, for this invention, neutralizing antibodies of ELA2A are selected.

In still another embodiment, ELA2A expression inhibitors may be selected from aptamers. Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. and Gold L., 1990. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consists of a conformationally constrained antibody variable region displayed by a platform protein, such as *E. coli* Thioredoxin A that are selected from combinatorial libraries by two hybrid methods (Colas et al., 1996).

Then, for this invention, neutralizing aptamers of ELA2A are selected.

Method of Screening for Treating Intestinal Inflammation and Pain

A further object of the invention relates a method for screening an ELA2A inhibitor (or antagonist) for use in the treatment or prevention of Inflammatory Bowel Diseases (IBD) or Irritable Bowel Syndrome (IBS) including Gluten hypersensitivity.

For example, the screening method may measure the binding of a candidate compound to ELA2A, or to cells tissue sample or organism expressing ELA2A, or a fusion protein thereof by means of a label directly or indirectly associated with the candidate compound. Furthermore, the screening method may involve measuring or, qualitatively or quantitatively, detecting ability of said candidate compound to inactivate ELA2A activity.

In a particular embodiment, the screening method of the invention comprises the step consisting of:

(i) providing purified ELA2A protein, providing a cell, tissue sample or organism expressing the ELA2A, (ii) providing a candidate compound such as small organic molecule, nucleic acids, antibodies, peptide or polypeptide, (iii) measuring the activity of the ELA2A, (iv) and selecting positively candidate compounds that, blocks the action of ELA2A or inhibits ELA2A expression.

In a particular embodiment, the screening method of the invention may further comprising a step consisting of administering the candidate compound selected at step d) to an animal model of Inflammatory Bowel Diseases (IBD) to validate the protective effects of said candidate compound.

In general, such screening methods involve providing appropriate cells which express ELA2A. In particular, a nucleic acid encoding ELA2A may be employed to transfect cells to thereby express the enzyme of the invention. Such a transfection may be accomplished by methods well known in the art. In a particular embodiment, said cells may be selected from the group consisting of the mammal cells reported yet to express ELA2A (e.g. epithelial cells).

The screening method of the invention may be employed for determining a ELA2A inhibitor by contacting such cells with compounds to be screened and determining whether such compound inactivates ELA2A.

According to a one embodiment of the invention, the candidate compounds may be selected from a library of compounds previously synthesised, or a library of compounds for which the structure is determined in a database, or from a library of compounds that have been synthesised de novo or natural compounds. The candidate compound may be selected from the group of (a) proteins or peptides, (b) nucleic acids and (c) organic or chemical compounds (natural or not). Illustratively, libraries of pre-selected candidate nucleic acids may be obtained by performing the SELEX method as described in documents U.S. Pat. Nos. 5,475,096 and 5,270,163. Further illustratively, the candidate compound may be selected from the group of antibodies directed against ELA2A.

ELA2A inhibition with the candidate compound can be tested by various known methods. For example Elastolytic activity assay (see Examples and FIG. 1) or (elastase inhibitor functional assay, see above) may be used for performing the screening method of the invention.

Method of Preventing or Treating Intestinal Inflammation and Pain

Another object of the invention is a method for treating a Inflammatory Bowel Diseases comprising administering to a subject in need thereof a therapeutically effective amount of a ELA2A inhibitor as disclosed above.

By a "therapeutically effective amount" is meant a sufficient amount of compound to treat and/or to prevent the Inflammatory Bowel Diseases or Irritable Bowel Syndrome (IBS).

It will be understood that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidental with the specific polypeptide employed; and like factors well known in the medical arts. For example, it is well within the skill of the art to start doses of the compound at levels lower than those required to achieve the desired therapeutic effect and to gradually increase the dosage until the desired effect is achieved.

The inhibitor of the ELA2A expression or ELA2A activity according to the invention can be administered by any suitable route of administration. For example, the inhibitor according to the invention can be administered by oral (including buccal and sublingual), rectal, nasal, topical, pulmonary, vaginal, or parenteral (including intramuscular, intra-arterial, intrathecal, subcutaneous and intravenous).

In an preferred embodiment of the invention, the therapeutic composition containing the ELA2A inhibitor is administered intrarectally or orally. A rectal administration preferably takes place in the form of a suppository, enema or foam. Intrarectal administration is particularly suitable for chronic inflammatory intestinal diseases which affect the lower intestinal sections, for example the colon.

Pharmaceutical Composition

The inhibitors of the present invention, together with one or more conventional adjuvants, carriers, or diluents may be placed into the form of pharmaceutical compositions and unit dosages.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

The pharmaceutical compositions and unit dosage forms may comprise conventional ingredients in conventional proportions, with or without additional active compounds or principles, and the unit dosage forms may contain any suitable effective amount of the active ingredients commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal administration; or in the form of sterile injectable solutions for parenteral uses. Formulations containing about one (1) milligram of active ingredient or, more broadly, about 0.01 to about one hundred (100) milligrams, per tablet, are accordingly suitable representative unit dosage forms.

The inhibitors of the present invention may be formulated in a wide variety of oral administration dosage forms. The pharmaceutical compositions and dosage forms may comprise compounds of the present invention or pharmaceutically acceptable salts thereof as the active component. The pharmaceutically acceptable carriers may be either solid or liquid. Solid form preparations include powders, tablets, pulls, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid, which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch gelatin, tragacanth, methylcellulose sodium carboxymethylcellulose, a low melting wax, cocoa butter, and the like.

The term "preparation" is intended to include the formulation of the active compound with an encapsulating material as carrier, providing a capsule in which the active component, with or without carriers, is surrounded by a carrier, which is in association with it. Similarly, cachets and lozenges are included. Tablets, powders, capsules, pulls, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavours, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavours, stabilizers, buffers, artificial and natural sweeteners, dispersants, thickeners, solubilising agents, and the like.

The inhibitors of the present invention may be formulated for parenteral administration (e.g., by injection, for example bolus injection or continuous infusion) and may be presented in unit dose form in ampoules, pre-filled syringes small volume infusion or in multi-dose containers with an added preservative. The compositions may take such forms as suspensions, solutions, or emulsions in oily or aqueous vehicles, for example solutions in aqueous polyethylene glycol. Examples of oily or non-aqueous carriers, diluents solvents or vehicles include propylene glycol, polyethylene glycol, vegetable oils (e.g., olive oil, and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The invention will be further illustrated by the following figures and examples. However, these examples and figures should not be interpreted in any way as limiting the scope of the present invention.

FIGURES

FIG. 1A-1B—Elastolytic activity is increased in epithelial cells from IBD colonic biopsies.

(a) In situ zymography of elastolytic activity in colonic mucosal biopsies from control groups (healthy) and from Crohn's disease (CD) patients taken in non-inflamed (NI) and inflamed area (I). (b) In cellulo zymography of elastolytic activity performed on epithelial cells in cultured after stimulation by LPS for 4 h. Images are representatives of three independent experiments. The intensity of enzymatic activity was illustrated using a pseudo-color gradient. Images are representatives of n=5 per group.

FIG. 2A-2C—ELA2A is expressed and secreted by colonic intestinal epithelial cells.

(a-b) ELA2A Immunostaining on longitudinal section (a) and on cross-section (b) of healthy area from human colonic resection. Signal of ELA2A is in green and signal related to epithelial cell marker, cytokeratin 18, is in red. (c) Immunostaining of ELA2A (green) and ELAFIN (red) on cross-section of healthy colon.

FIG. 3A-3B—ELA2A expression is increased in IBD colonic epithelial layer.

(a) ELA2A immunostaining on cross section of colonic biopsy from healthy controls, non inflammatory (NI_IBD) and inflammatory (I_IBD) areas from IBD patients using anti-ELA2 and anti-EPCAM antibodies, the latest being representative of the epithelial compartment. (b) Quantification of ELA2A signal in healthy controls (n=5) versus noninflammatory (NI_IBD) and inflammatory (I_IBD) areas from IBD patients (n=9). Data represent the intensity of ELA2A signal per unit of epithelial surface. *p<0.05; ** p<0.001 compared to healthy patients using 1-way ANOVA with Bonferroni post-test.

FIG. 4A-4D—Expression and localization of ELA2A in intestinal epithelial cells and in vivo: effect of inflammatory stimuli or microbiota exposure.

(a) ELA2A immunostaining on polarized Caco-2 cells cultured on transwell. Orthogonal view of Caco-2 cell monolayer showing ELA2A staining in green and actin network in blue. (b) Western blot analysis of ELA2A in the conditioned medium and cytoplasmic fraction of Caco-2 cells. (c) Immunofluorescence of ELA2A after LPS or TNFa-treatment of Caco-2 cells. Polarized Caco-2 cell monolayer was treated by 50 µg/mL LPS at the apical side or 10 ng/ml TNFa at basolateral side for 24 hours. (d) ELA2A immunodetection on cryo-sections from normal, 5% DSS-treated during 5 days and germ-free mouse colons. Nuclei are stained by DAPI (blue signal). Results are representatives of three independent experiments.

FIG. 5A-5E—Over-expression of ELA2A in Caco-2 cells disrupts epithelial barrier function.

(a) Paracellular permeability measurements in control versus ELA2-overexpressing (Tg-ELA2) Caco-2 cell monolayer. The graph indicates the fold increased in dextran flux of Tg-ELA2 cells compared to control cells. * p<0.001 for all comparison using two tailed t-test, n=16 per group. (b) Bacterial translocation through control and Tg-ELA2A monolayer was assayed (n=12 per group).  p<0.01 using two tailed t-test. (c) Immunofluorescence staining of CLAUDIN-1, ZO-1 and F-ACTIN performed on control and ELA2A-overexpressing Caco-2 cell monolayer. (d) Protein levels of tight junction proteins OCCLUDIN, CLAUDIN-1 and ZO-1 were assessed by Western blot analysis in insoluble and soluble fraction of protein extraction from control and Tg-ELA2A monolayer. Blot are representative of 3 independent experiments with n=3 per group. Quantification analysis was performed and data are the mean±SEM of 3 experiments with n=3 per group;  p<0.01; * p<0.001 by 1-way ANOVA with Bonferroni post-test. (e) FITC-Dextran flux after incubation of recombinant human ELA2 on the apical medium of polarized Caco-2 monolayer. ELA2 at various concentrations (0.001, 0.01 and 0.1 U·ml-l) were added to the apical side of Caco-2 cells for 24 h. Data are the mean of 3 independent experiments with n=3 per group. * p<0.05 by 1-way ANOVA with Bonferroni post-test.

Figure 6A:
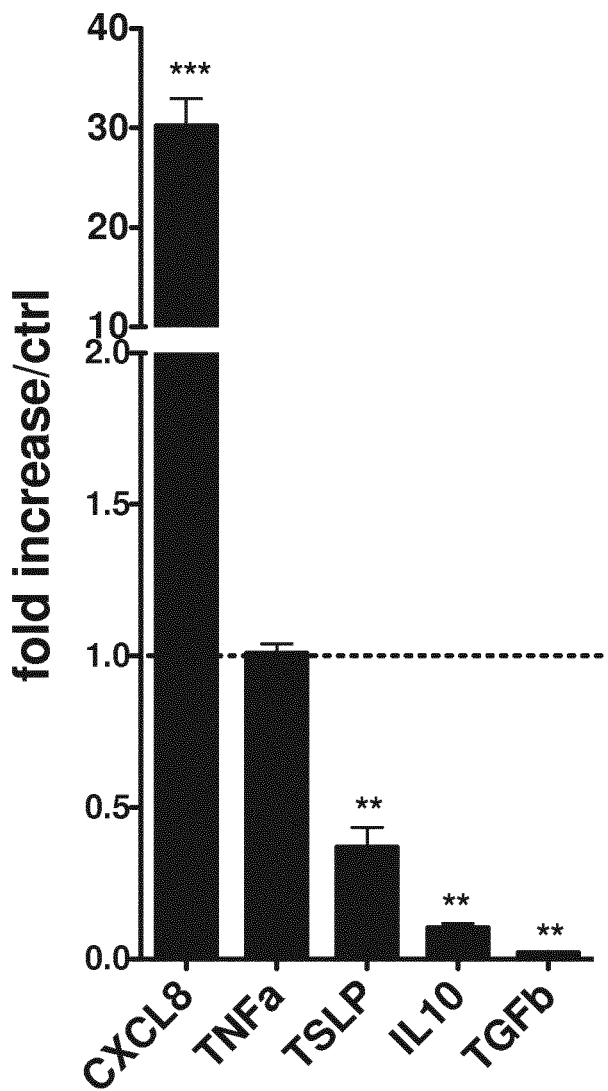
Figure 6:
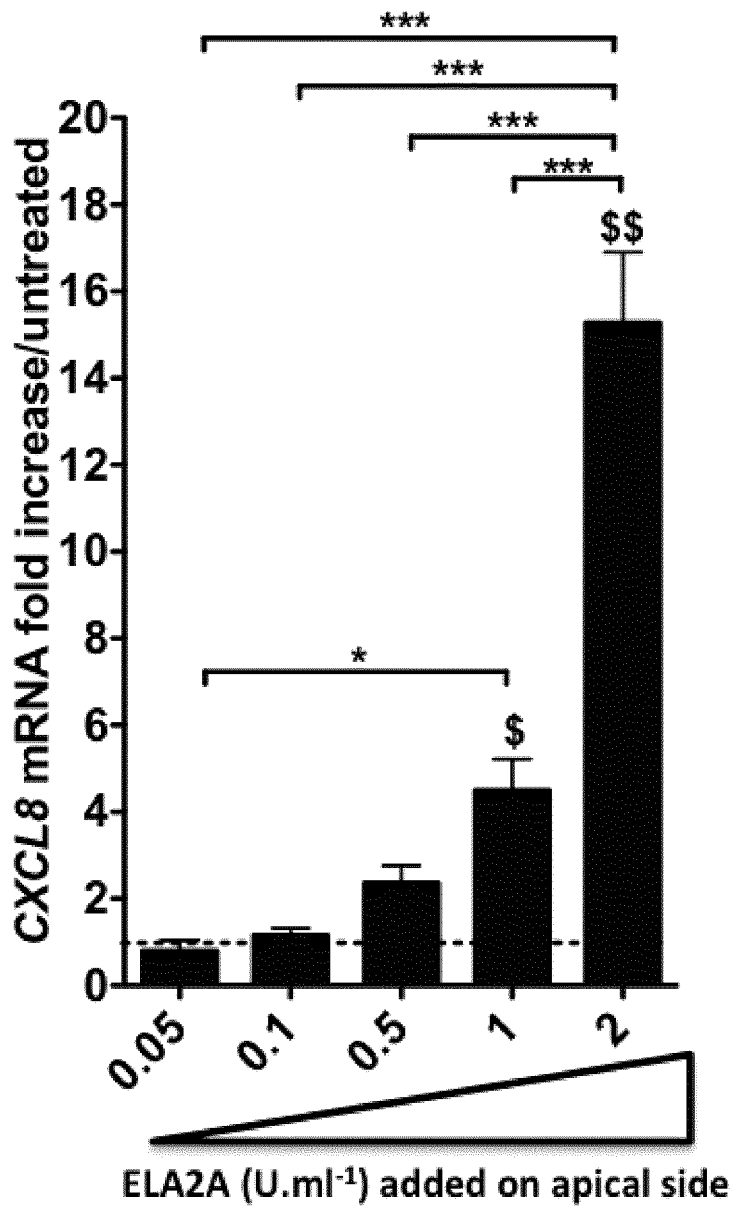

FIG. 6A-6B—Increase amount of ELA2A in extracellular compartment of Caco-2 cells induces change of cytokine expression's profile.

(a) Pro-inflammatory cytokines quantification in ELA2A-overexpressing Caco-2 cells. The graph indicates the fold increase of the different cytokines in Tg-ELA2A versus control, after normalization to HPRT housekeeping gene. Data are expressed as mean±SEM of n=3 for each group in 3 independent experiments, p<0.01, *p<0.001 compared to control using two tailed t-test. (b) Quantification of CXCL8 transcripts after stimulation of Caco-2 monolayer by different concentrations of recombinant ELA2A. Data are expressed as mean±SEM of n=3 for each group in 3 independent experiments, $p<0.05, $$p<0.01, compared to control p<0.01, *p<0.001 for all comparisons indicated by the bracket using 1-way ANOVA with Bonferroni post-test.

FIG. 7A-7F—Effects of ELA2A overexpression after colonic injection of ELA2-encoding adenovirus in mice.

(a) HA immunostaining (green) on colonic tissue from mice receiving adenovirus containing CELA2A cDNA fused to HA tag. ZO-1 staining is represented in red. (b) In situ zymography of elastolytic activity in colon from mice receiving Ad-null or Ad-ELA2A during 2% DSS treatment. (c-e) The macroscopic damage score (c), colon wall thickness (d), and microscopic damage score (e) in mouse colon tissue was determined. Pooled data are from two independent experiments (n=6 per group). *p<0.05, p<0.01, *p<0.001 compare to control, $<0.05, $$<0.01 compared to DSS+PSS condition, φ<0.05, φ<0.0001 compare to DSS+Ad-null using one-way ANOVA or using Kruskal Wallis and subsequent Dunn's multiple comparison test when appropriate. (f) Representative immunofluorescence staining (n=8 mice in each group) for macrophages stained with anti-F4/80 (red). Quantification of staining intensity in both groups was expressed as fluorescence intensity per unit of tissue's surface. ** p<0.01 using two-tailed T-test.

Figure 8:
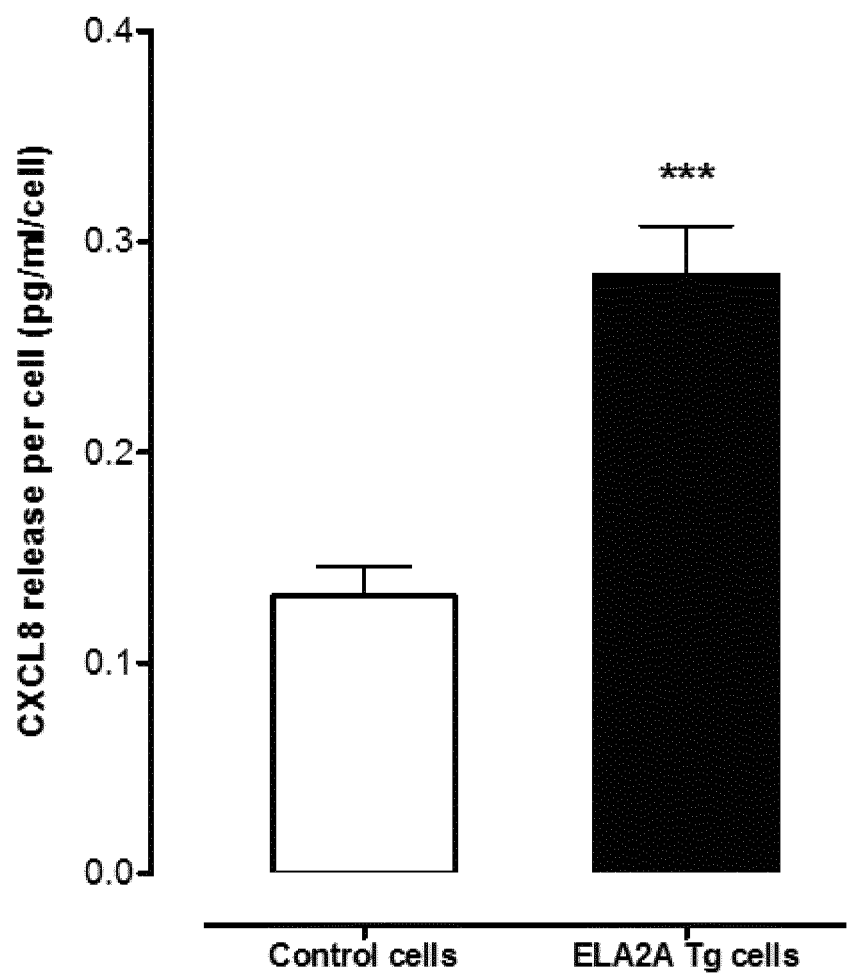

FIG. 8—ELA2 over-expressing intestinal epithelial cells increase the release of CXCL8 protein compared to control cells.

Figure 9:
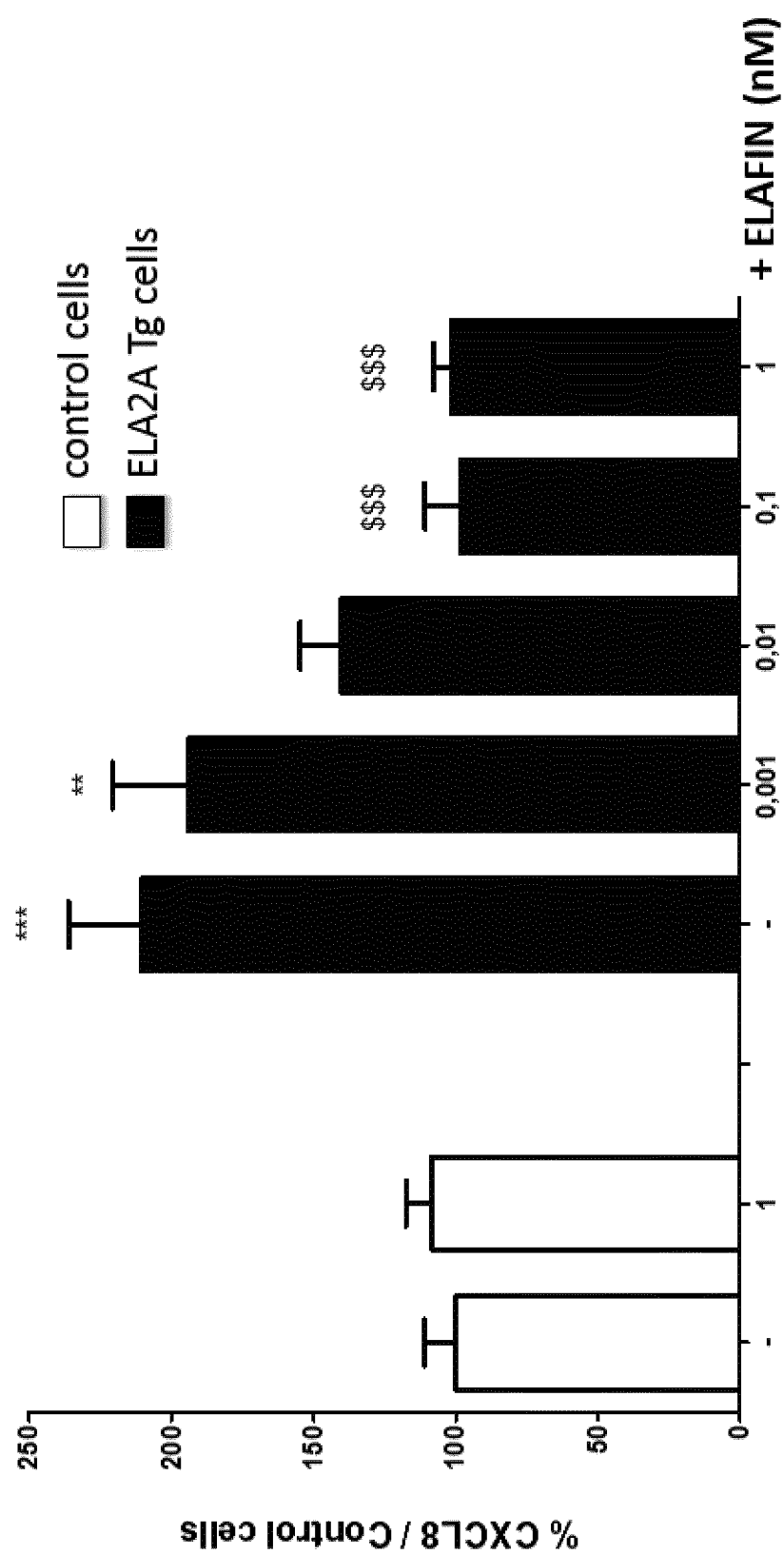

CXCL8 protein release after 24 h of culture, dosed by ELISA in supernatants from wild type intestinal epithelial cells (Caco-2) (control cells) or in supernatants of Caco-2 cells transgenic for overexpressing ELA2A protein. *** different from control cells for p<0.0005, student's t test FIG. 9—The increased CXCL-8 protein release observed in ELA2A Tg cells (cells overexpressing ELA2A) is inhibited by ELAFIN addition to the culture, in a dose-dependent manner.

Percentage of CXCL8 protein release compared to control cells (wild type Caco-2) in wild-type Caco-2 cells (control cells) or in Caco-2 transgenic cells overexpressiong ELA2A, exposed or not (-) for 24 h to different doses of ELAFIN. CXCL8 protein was dosed in cell culture supernatants by ELISA. ANOVA analysis was performed, * and different from control cells for p<0.0005 and p<0.005 respectively. $$$ different from ELA2A transgenic cells non-exposed to ELAFIN.

EXAMPLE 1: MATERIAL & METHODS

Patients

Human colonic tissues were obtained from individuals treated at the Centre Hospitalier de Toulouse (France). Biopsies were collected during colonoscopy procedures aimed at clinically evaluating the disease of established and well-characterized CD and UC patients or they were realized in individuals undergoing colon cancer screening who were otherwise healthy (here, healthy controls). The written and verbal informed consent was obtained before enrolment in the study, and the Ethics Committee approved the human research protocol (ClinicalTrials.gov Identifier: NCT01990716). Clinical information on the patients is compiled in supplementary table 1.

Fresh biopsies were rinsed in isotonic sterile Hanks' balanced salt solution (HBSS) and were then immediately incubated in 2 ml HBSS at 37° C. for 1 hour. Isolated biopsy specimens were embedded in optimal cutting temperature (OCT) compound (Dako) at −186° C. and stored for in situ elastolytic activity.

Cell Culture

Human colonic epithelial (Caco-2) cells (American Type Culture Collection, Manassas, Va.) were grown in Glutamax DMEM (Invitrogen, Cergy-Pontoise, France). The media was supplemented with 10% heat-inactivated fetal bovin serum (Invitrogen), 100 U/100 ug/mL penicillin/streptomycin (Invitrogen) and 1% non-essential amino acids (Sigma). Cultures were kept at 37° C. in a 5% $CO_2$ and 96% humidity environment, and culture medium was replenished every 2-3 days. Confluent cells were sub-cultured after $Ca2+/Mg2+$-free PBS washes and partial digestion with trypsin (Sigma). Cells were grown to confluence on culture-treated plates (Becton Dickinson, Sparks, Md.), or Transwell filter units with semipermeable filter membranes (0.4- to 1.0-um pores; Corning, N.Y., US). At the time of treatment, Caco-2 monolayers were incubated in OptiMEM medium.

For some experiments, Caco-2 monolayers were incubated with purified LPS (50 µg/mL), TNFa (concentration, marque) or substance P (concentration, marque) for 24 h.

Caco-2 monolayers were treated with recombinant ELA2 at various concentrations (0, 0.001, 0.01 or 0.1 U·ml-l) in apical compartment for 4 h. As control, ELA2 was pretreated for 15 min with chemical protease inhibitors ELAFIN (R&D) or AEBSF (sigma).

In Situ Zymography

Frozen OCT sections of colonic tissues from patients and mice (8-um thickness) were rinsed with a washing solution (2% Tween-20) and incubated at 37° C. for 6 h with Bodipy-FL-Elastin (0.5 mM) by the EnzChek Elastase Assay Kit (Invitrogen) according to a previously published protocol (13). All sections were visualized with the LSM710 microscope (Carl Zeiss France) and were analyzed by observers blinded of the treatments, with Zen 2009 software (Carl Zeiss).

Elastolytic Activity Assay

Elastolytic activity was measured with Bodipy-FL-Elastin (0.5 mM) as substrate. Samples were resuspended in buffer (50 mM Tris-HCl, 500 mM NaCl, and 0.1% Triton X-100). The change in fluorescence (excitation, 485 nm; emission, 530 nm) was measured over 30 min at 37° C. on a microplate reader NOVOstar (BMG Labtech) to calculate the rate of Elastin degradation.

Immunostaining

Cryosections of 5 um, or transwell filter with epithelial cells were fixed Nonspecific binding sites were blocked with 1% BSA in PBS for 30 min and then incubated overnight at 4° C. with primary antibody in blocking buffer (Santa Cruz Biotechnology). Following antibody anti-ELA2 (1/200; SantCruz), anti-ELAFIN (1/500; Santa Cruz Biotechnology), anti-Epcam (1/200 dilution; from Abcam), anti-F4/80 (1/100 dilution, from AbD Serotec) or Ly-6G (1/400 dilution, from AbD Serotec) were used for immunohistochemistry on tissue.

Cells were incubated in 1% BSA in PBS with primary antibodies as follows: anti-ZO-1 (1:250 dilution; from Invitrogen), anti-CLAUDIN-1 (1:250 dilution; from Invitrogen), anti-ELA2 (1/200 dilution; from Sigma-Aldrich), phalloidin (1/50 dilution; from Molecular probes).

Anti-mouse, anti-rabbit or anti-goat coupled with Alexa Fluor 555-, and anti-mouse Alexa Fluor 488-conjugated secondary antibodies (1:1000 dilution; all from Invitrogen) were used.

Slides were mounted and nuclei were stained with DAPI fluorescent mounting medium (Invitrogen) and analyzed on a confocal microscope (Zeiss LSM710, Carl Zeiss) by observers unaware of treatments. Images representative of each group were selected.

Epcam staining was used to estimate the epithelium surface on each cryosections of biopsy. For each patient, 8 images were obtained, intensity of ELA2 staining and epithemium surface were quantified using image J software.

For mouse study, DAPI was used to estimate the total tissue surface. Histograms represented the mean of four different fields per animal (n=8 animals per group)

RT-PCR Analysis

RNA was isolated using the RNeasy kit (QIAGEN). 1.5 to 5 µg RNA were reverse transcribed following the recommendations of the Superscript first strand synthesis system. PCR was performed with GoTaq polymerase (Promega), using 1/10 to undiluted cDNA as a matrix, with primers indicated in Supplemental Table 2. If needed, amplicons were cloned into pGEMT-easy (Promega) and then sequenced using Big Dye Terminator.

Levels of specific mRNA transcripts were determined by qPCR using SYBR Green PCR Master Mix and was performed on a LightCycler 480 (Roche Diagnostics). Relative expression of targeted genes was compared to hypoxanthine phosphoribosyltransferase expression.

Construction and Selection of ELA2A Transgenic Caco-2 Cell Line

Human cDNA encoding ELA2A was amplified by RT-PCR and introduced in pwpxLD vector, downstream to the promoter EF1-α as a second exon with GFP in first (sup FIG. 2)

Genetically modified cells were isolated by cell sorting considering GFP expression. ELA2A over-expression was confirmed by qPCR and western blot.

Western Blot

Cultured cells were crushed in a protein extraction buffer (PEB) containing 50 mM Tris-HCl, pH 8.0, 120 mM NaCl, 5 mM EDTA, 0.5% Nonidet-P40, and 1× Protease Inhibitor Cocktail Tablets (EDTA-Free; Roche) with Ultra-Turrax. Total lysates were sonicated 3× for 5 s and were clarified from insoluble material by centrifugation at 12.000 g, 4° C. for 30 minutes.

Cellular fractions (soluble and insoluble) were obtained by cellular lysis in 1% Triton X-100, 100 mM NaCl, 10 mM HEPES, pH 7.6 mM EDTA and 1× Protease Inhibitor Cocktail Tablets (EDTA-Free; Roche) and were prepared according to Jacob et al. (31). Briefly, lysates were centrifuged at 15.000 g, 4° C. for 30 minutes and the supernatant formed the soluble fraction. The pellet was sonicated in Triton buffer containing 1% SDS and centrifuged at 15.000 g, 4° C. for 5 minutes to obtain the insoluble fraction.

Protein content was quantitated and equal amounts (50 ug) were separated by SDS-polyacrylamide gel electrophoresis (7-15%) and transferred to nitrocellulose membrane (Whatmann, VWR International). Membranes were blocked in Tris-buffered saline with 5% nonfat dry milk and 1% BSA. Blots were incubated with a primary antibody overnight at 4° C. Following primary antibodies were used; rabbit (1:500 dilution; from Sigma-Aldrich) or goat anti-ELA2 (dilution 1:200; from Santa Cruz), rabbit anti-OCCLUDIN (1:500 dilution; from Invitrogen), rabbit monoclonal anti-CLAUDIN-1 (1:250 dilution; from Invitrogen), and anti-ZO-1 (1:250 dilution; from Invitrogen); mouse monoclonal anti-b-Actin (1:10000 dilution; from Sigma-Aldrich) and anti-Vinculin (1:5000 dilution; from Sigma-Aldrich). Mouse, rabbit or goat horseradish peroxidase-conjugated secondary antibodies (1:3000 dilution; both from Cell Signalling Technology) were used 1 h at room temperature and then blots were visualized by chemiluminescence on (BioRad). Signal density was calculated using Image Lab software (Biorad). Actin was used as a loading control for total and soluble fraction and Vinculin as control for insoluble fraction.

Permeability Measurements

Caco-2 cells (2.105 cells/well) were cultured in monolayer in 12-well Transwell plates (Corning Life Sciences) (0.9-1.12 cm2 surface area) until confluence. After 21 days of culture (reaching transepithelial resistance >500Ω×cm2), cells were rinsed with PBS solution and Optimem medium (Life Science) was added into apical and basolateral chambers.

To assess epithelial permeability, FITC-dextran (4 kDa, 100 g/ml) was added to the apical compartment of the Transwells up to 4 h. Basolateral samplings were taken at each sample time-point. The apical-to-basolateral flux of FITC-dextran was measured on a fluorescence plate reader (NOVOstar, BMG Labtec) with an excitation wavelength of 496 nm, emission at 524 nm, and a cut off of 515 nm. Paracellular permeability to dextran-fluorescein isothiocyanate was expressed in nM of dextran-fluorescein isothiocyanate.

To analyse bacterial translocation into Caco-2 and Tg-ELA2 cells, *Escherichia coli* K-12 strain (Alexa Fluor 488, Life Technology) was added at 1×107 CFU/mL into apical compartment of transwell inserts. Permeability was evaluated by sampling the basolateral content 12 h after *E. coli* addition in the apical compartment.

Heterologous Elastase Expression and Purification

Human form of CELA2A cDNA was subcloning in pCineo vector (Promega) with HA-tag in fusion in C-term of encoding ELA2 sequence.

This plasmid was transfected into CHO-Ki cells (ATCC® CCL-61™) using Genejuice transfection reagent according to the manufacturer's instructions (Merck). The cells were selected with G418 (Invitrogen SARL) at 1.6 mg ml-1 during 10 days in medium HAMF12, 10% SVF, Non Essential amino acid. The cells were grown in medium with G418 (0.8 mg ml-1). Before harvesting medium, cells were washed with PBS 5 times and replaced by Optimem (Invitrogen SARL). Optimem medium were collected 48 h later containing pro-ELA2AHA.

ELA2AHA was purified using affinity column for HA epitope following manufacturer's instruction. Heterologous protein was eluted using 3M NaSCN and pH was immediately neutralized. Pro-ELA2AHA was activated with Trypsin-Agarose (Thermo Scientific™ Pierce™) for 90 min at 37° C. Trypsin activity released from agarose was blocked using Activity Based Probe coupled with biotin and eliminated using streptavidin resin following manufacturer's instructions (GE Healthcare life science). After centrifugation, active ELA2AHA was collected into the supernatant and elastolytic activity was quantified.

Adenovirus Constructs

The coding sequence of hCELA2A fused to a HA epitope tag was inserted by directional cloning into pShuttle/CMV, thus generating the transfer vector pShuttle/CMV-hCELA2A-HA. Recombination of pShuttle/CMV-hCELA2A-HA with the serotype 5 adenoviral backbone plasmid pVQAd/9.2-100/RSV-eGFP and production of adenoviral particles, were performed by Viraquest (North Liberty, Iowa, USA), as previously described (32). The control adenovirus VQAd/CMV-eGFP was acquired from Viraquest. The adenoviruses VQAd/CMV-hCELA2AHA/RSV-eGFP and VQAd/CMV-eGFP (herein renamed as Ad-ELA2A and Ad-null respectively) were concentrated and purified to 5×1010 plaque forming units (pfu) per mL.

Animals and Induction of Colitis

Male BALB/c mice (6-8 weeks) were from Janvier (Le Genest Saint Isle, France). All animals were maintained under 12-hour light-dark cycles with free access to food and water, except for being fasted the day before the intracolonic injection of adenovirus. Experimental procedures were approved by institutional animal care committees. Animals pre-treated for 3 days with 2% DSS were anaesthetised (ketamine and xilazine, respectively at 80 and 20 mg/kg, i.p.) and then submitted to an intracolonic injection of 1×109 pfu of Ad-ELA2A or Ad-null. Control or DSS-treated mice received an intracolonic injection of vehicle, 100 µL of phosphate-buffered saline, as a control procedure of adenovirus intracolonic injection. Body weight and hydration status were followed up on a daily basis throughout the whole course of experiments. Animals were kept under DSS treatment for four additional days after the intracolonic injection of adenovirus. Then mice were sacrificed and colons were harvested for measurement of inflammation parameters macroscopic damage score, bowel thickness, microscopic damage score, MPO activity, elastolytic activity, and immune cells infiltration as previously described (5, 8). Alternatively, some animals were killed two days after the intracolonic injection of adenovirus in order to verify the recombinant expression of hCELA2A by RT-PCR and immunostaining.

EXAMPLE 2: RESULTS

Elastase Activity is Detected in Intestinal Epithelial Cells

Considering the increased elastolytic activity detected in colons of IBD patients both in inflamed and non-inflamed parts of the tissues, we investigated the cellular source of elastolytic activity in human colons using in situ zymography. Within the gut section from healthy individuals, elastase activity was detected in the epithelium only (FIG. 1a). In colonic tissue slices from Crohn's disease (CD) patients taken in inflammatory areas, elastolytic activity was largely increased compared with tissues from otherwise healthy controls (FIG. 1a). The strongest activity was still localized in epithelial cells. To a lesser extend, elastolytic activity was also present in the submucosa of CD inflamed tissues, associated with infiltrated granulocytes. In non-inflamed colonic mucosa from IBD patients, epithelial cells also represented the main source of elastolytic activity and the intensity was similar to that observed in inflamed mucosa (FIG. 1a). To confirmed elastolytic activity into epithelial cells, we performed in situ elastolytic zymography in cultured intestinal epithelial cells (IEC, Caco-2). In pro-inflammatory condition, those cells (LPS exposure) also exhibited elastase activity (FIG. 1b).

ELA2A is a Protease Expressed by Colonic Epithelial Cells

To determine the identity of elastase form(s) expressed in IEC, RT-PCR was performed with mRNA from Caco-2 cells and specific oligonucleotides to investigate the expression of the 5 known human elastase genes (ELAN, CELA1, CELA2, CELA3 and MMP12). RT-PCR analysis revealed a single transcript of CELA2A, and sequencing revealed 100% identity to the full-length cDNA from CELA2A gene (NCBI accession number NM_033440; Swiss-Prot accession number P08217, ELA2A as protein name). We also showed transcriptional expression of its orthologous Cela2A in murine colon.

ELA2A expression was then highlighted by immunostaining in colonic tissues. Signal corresponding to ELA2A was observed along the colonic crypt suggesting that ELA2A is produced by all cell types of colonic epithelial cell (FIG. 2a). On cross-section, staining was seen in the lumen, implying that epithelial cells secrete ELA2A (FIG. 2b).

It has been previously described in the skin, that ELA2A activity is tightly controlled by ELAFIN, which is an elastase inhibitor (13). To confirm possible interaction between ELA2A and ELAFIN in colonic tissues, we performed double-labelling experiments. ELA2A and ELAFIN colocalized in colonic epithelial cells as shown by immunofluorescence analysis in colonic tissues from healthy controls (FIG. 2c). ELA2A staining was observed throughout the cytoplasm, with areas of accumulation at the membrane level. ELAFIN staining appeared as dots in cytoplasm and also concentrated in the plasmatic membrane. Furthermore, ELA2A and ELAFIN stainings overlapped at the membrane level and as dots in the cytoplasm as well outside of the cells in the lumen (FIG. 2c), thus supporting the concept of a direct interaction between both proteins in the colonic mucosa.

Localization and Regulation of ELA2 Expression in Intestinal Epithelium

ELA2A expression was studied in colonic mucosa of IBD patients. Despite the epithelial cell erosion associated with inflammation, ELA2A staining was still observed in remaining epithelial cells from IBD tissues (FIG. 3a). Relative quantity of ELA2A among patients was quantified using co-immunostaining with an epithelial cell marker permitting to delineate the epithelium's surface. Quantitative analysis showed that in epithelial layer ELA2A amount was 2 fold increased in IBD tissues compared with tissue from healthy donors (FIG. 3b). This significant increase was in the same order of magnitude in inflamed or non-inflamed mucosa. Therefore the increased expression of ELA2A seems to be independent from the inflammatory status of the colon in IBD patients.

We next investigated the expression of ELA2A in cultured IEC (FIG. 4a). Analysis of ELA2A localization showed that in IEC monolayers, ELA2A signal was concentrated at the membrane level. Transversal view of cells evidenced that ELA2A-immunoreactivity was closely associated to the plasma membrane, both at apical and basolateral sides.

In agreement with the presence of peptide signal on primary sequence of ELA2A, western blot analysis revealed that this protease was mainly secreted in the extracellular medium (FIG. 4b).

Considering the up-regulation of ELA2A expression in IBD condition, we investigated potential stimuli that could regulate its expression in intestinal epithelial cells. IFNg, IL1b, and substance P added to culture media had no effect on CELA2A gene transcription (data not shown), LPS as well as TNFa presence in the medium induced a significant increase of ELA2A amount in the cytoplasm (FIG. 4c). ELA2A signal was mainly concentrated in the junctional areas in untreated cells but LPS and TNFa treatments promoted an increased expression of ELA2A all along the cell junctions and in the cytoplasm areas as well. mRNA quantification revealed that CELA2A transcripts were 6-fold augmented with LPS.

To further evaluate the regulation of ELA2A expression during inflammation, ELA2a immunostaining was performed on colonic slices from mice submitted to DSS-induced colitis (5%; 7 days). In colonic tissues from control or DSS-induced colitis animals, ELA2A-immunoreactivity was restricted to epithelial cells, and under inflammation, ELA2A staining was increased (FIG. 4d). In contrast, ELA2A was absent from the colonic tissues of germ-free mice, thereby strengthening the potential role of microbial components in driving ELA2A expression.

ELA2A Up-Regulation Alters Epithelial Barrier Function

Next, we studied the consequences of ELA2A hyperactivity of different actors of epithelial barrier function. For this purpose, we have developed ELA2A transgenic Caco-2 cells, which constitutively over-expressed human CELA2A. Analysis of transcriptional levels revealed that the integrated construction allowed a 200-fold CELA2A over-expression, compared to control Caco-2, which was genetically transformed to constitutively express GFP only (data not shown). Western blot analysis confirmed ELA2A over-expression in intestinal epithelial cells. Additionally, Western-blot showed that ELA2A was mainly released in apical culture media of epithelial cells. Measurement of proteolytic activity showed that elastolytic activity released in the culture medium was 2-fold increased compared to control Caco-2 cell line. These cell lines did not present an increase of cell death as caspase-3 amounts were similar in control and Tg-ELA2A cells. Quantity of alkaline phosphatase was similar between both cell lines indicating that epithelial cell differentiation was not disturbed by ELA2A hyperactivity.

Paracellular and transcellular routes through the epithelial monolayer were investigated by measuring the flux of FITC-labelled 4-kDa dextran and the translocation of killed fluorescent E. coli, respectively. Both fluxes from the apical to the basolateral side were greatly enhanced in Tg-ELA2A cellular monolayers, compared to control cells (FIGS. 5a and b). As the diffusion of these tracers is controlled by TJ function, TJ's integrity was assessed by immunocytochemistry and western blot. The immunoreactivity of CLAUDIN-1 appeared as a fine line delimiting plasma membrane in wild-type cells whereas staining in Tg-ELA2A cell borders diminished and appeared particulate (FIG. 5c). Control colonic Caco-2 monolayers displayed ZO-1 distribution in a characteristic tortoise-shell staining pattern (FIG. 5c). In Tg-ELA2A monolayer, ZO-1 staining was decreased at the membrane level and appeared as dots or clusters. No specific increased staining was detected in the cytoplasm. The perijunctionnal F-actin was connected with TJ and detected as a fine ring-like structure in the perimeter of the apical pole of control epithelial cells. In contrast, in ELA2-overexpressing Caco-2, F-actin signal appeared as a large bandeau revealing a disorganization of the actin network (FIG. 5c). Compared to control cells, ELA2 hyperactivity induced a significant decrease in OCCLUDIN, CLAUDIN-1 and ZO-1 protein expression in insoluble fractions as well as cytosolic fractions for OCCLUDIN and ZO-1 (FIG. 5d). Concomitantly, upon ELA2A overexpression, mRNA levels were either not modified for OCCLUDIN and ZO-1, or slightly (3-fold) increased for CLAUDIN-1. These data argue against a mechanism involving junction protein translocation induced by ELA2A and are rather in favour of an ELA2-induced TJ protein degradation.

To confirm a direct effect of ELA2A on epithelial cells, we exposed wild-type Caco-2 monolayers to exogenous purified ELA2A and we analysed barrier function 4 hours after treatment. Apically applied ELA2A induced a significant and dose-dependent increase of dextran flux through the monolayer (FIG. 5e). Pre-incubation of ELA2A with ELAFIN or the chemical serine protease inhibitor AEBSF, abolished the loss of barrier function, demonstrating that ELA2A elastolytic activity is responsible for increased permeability. OCCLUDIN, CLAUDIN-1 and ZO-1 membrane protein expression were also significantly reduced by increasing doses of exogenously applied ELA2.

ELA2A Controls Inflammation-Associated Epithelial Genes

Cytokine profile expression was analysed in ELA2A-overexpressing Caco-2 cells, compared to wild-type Caco-2. The quantity of transcripts encoding TNFa was unchanged in ELA2A transgenic epithelial cells compared to wild-types. ELA2A hyperactivity induced a major up-regulation of CXCL8 transcripts (FIG. 6a). In contrast, mRNA amount of cytokines involved in epithelial homeostasis such as IL10, TGFb and TSLP were dramatically decreased in comparison to control cells (FIG. 6a).

In order to confirm a direct effect of ELA2A on epithelial cells, as opposed to the consequences of prolonged signalling pathways in transgenic cells over-expressing ELA2A, we analysed cytokine's profile from wild-type epithelial cells, 4 hours after the exogenous addition of ELA2A to the apical side. In this experimental condition, CXCL8 was upregulated in a concentration dependent way, while TNFa, TGFb, IL-10 and TSLP transcript levels remained unchanged (FIG. 6b), thus highlighting that CXCL8 upregulation is a first event consequently to ELA2A hyperactivity in the extracellular space.

In Vivo, ELA2 Over-Expression Worsens Inflammation

To investigate the effects of ELA2A hyperactivity on colonic homeostasis in vivo, adenovirus encoding the human form of ELA2A was injected into the colonic lumen of mice. To favour the entry of adenovirus into the colonic cells, mice were beforehand treated with a low dose of DSS (2%) during 3 days. RT-PCR achieved with primers specifically targeted the human CELA2A-HA mRNA confirmed that adenovirus permit the expression of CELA2A-HA in colon (sup FIG. 5b). Immunostaining against the HA tag performed on colonic section from mice receiving ELA2A adenovirus revealed the presence of exogenous ELA2A into the epithelial cells (FIG. 7a), five days after adenovirus injection. In situ zymography performed on colonic sections from mice receiving CELA2A-expressing adenovirus revealed an increase of elastolytic activity mainly concentrated to the epithelial cells compared to mice receiving Ad-null (FIG. 7b). Concomitantly, elastolytic activity in colonic wash was 4-fold increased compared to control mice (Ad-null condition) in mice receiving CELA2A-expressing adenovirus (sup FIG. 5c).

Mice treated with 2% DSS for 7 days developed a mild degree of colitis, as characterized by an increase in macroscopic damage score and colonic wall thickness, while microscopic damage score did not increased significantly. Beside, mice submitted to DSS-induced colitis and injected with Ad-ELA2A developed a more pronounced colitis. They presented an increased macroscopic damage score (FIG. 7c), enlarged colonic wall thickness (FIG. 7d) and augmented microscopic damage score (FIG. 7e), once compared to mice from control group or DSS-induced colitis groups injected with PBS or Ad-null. Tissue changes associated to colitis in Ad-ELA2A-injected mice were more obvious at distal colon, wherein an increase of adhesion points, oedema, erythema and mucus secretion were observed compared to mice treated with GFP adenovirus (Ad-null). In contrast, proximal colon and small intestine were not affected in these experimental conditions. Histological analysis revealed that ELA2A over-expression induced an increase of mucosal damage (1.5-fold compared to tissues from mice treated with Ad-null), although not statistically significant (FIG. 7e). No significant increase in MPO activity was observed in colons of CELA2A-adenovirus-treated mice compared to controls. The absence of neutrophil influx was confirmed by immunostaining with a specific marker of neutrophils (sup FIG. 5f). By contrast, there was an increase of macrophage infiltration within the colonic lamina propria (FIG. 7f) of Ad-ELA2A injected mice, since staining for the F4/80 marker increased 2.3 fold in these animals in comparison to Ad-null mice.

Discussion

In recent years the understanding of the pathogenesis of Crohn's disease (CD) and ulcerative colitis (UC) has made enormous progress. The importance of the mucosal barrier for preventing bacterial invasion and subsequent inflammation has been shown in genetic studies identifying risk genes and animals models (14-16). Increased epithelial permeability plays a central role in inflammatory processes. This impaired permeability reflects a primary defect of the tight junctions between epithelial cells (17, 18). This concept has recently gained some supports as studies using confocal endoscopy have identified an increased frequency of mucosal breaks in the endoscopically healthy mucosa of IBD patients (19, 20). With this in mind, a large part of basic research has focused on cytokines to highlight their role in their capacity to initiate and maintain the epithelial barrier's dysfunction.

In our study disclosed that elastase activity is localised in colonic epithelial cells. Epithelial cells produced a low level of elastase activity at steady state and this activity is increased in colonic inflammatory condition. In situ zymography revealed that those cells represent the major source of elastase activity in inflamed areas of IBD colon, as well as in non-inflamed zones. This suggests that intensification of epithelial elastolytic activity could constitute one of the first steps of epithelial injury, and particularly, one of the initial events of barrier dysfunction associated with IBD. Looking for the source of this elastolytic activity, our results demonstrate that colonocytes released an elastase named ELA2A. Although they bear the same generic name, elastase from neutrophil (ELANE) and ELA2A are two proteases distinct proteases. They share only 26% of amino acid identity. ELA2A has enzymologic properties similar to those of chymase (chymotrypsin-like activity), with elastase-like activity. Both enzymes cleave ELASTIN, but human leukocyte elastase preferentially cleaves ELASTIN at valine residues, while ELA2A hydrolyzes ELASTIN at leucine, tyrosine, and phenylalanine bonds and prefers proline to alanine in the P2 position from the cleaved bond into substrate (21). Therefore, it is reasonable to think that these two enzymes have different functions and specificity, and that particularly in the context of inflammation, they might have different substrates. This study identified unambiguously ELA2A as a protease produced by colonic epithelial cells for the first time. Previous study focused on genes of interest in a susceptibility to IBD including proteases and proteases inhibitor didn't highlighted ELA2A as protease involved in IBD since CELA2 gene was not included into the study (22).

The ELA2A quantity is increased in IBD epithelium independently of the inflammatory status of colonic tissues, compared to healthy tissues. This is concomitant with elevated elastolytic activity measured in culture supernatants of biopsies harvested from both inflamed and non-inflamed areas of the colon of IBD patients, compared to supernatants of biopsies from healthy controls (5). As ELA2A is secreted by epithelial cells, this protease could participate to elastolytic activity measured in supernatants of colonic biopsy. In addition, intestinal epithelial cells also express ELAFIN, which is a potent ELA2A inhibitor (13). Co-immunolocalisation of ELA2A and ELAFIN shows that both proteins are secreted together in the colonic lumen. However, in IBD conditions, ELAFIN expression is abolished in epithelial cells (5). Therefore, the absence of endogenous inhibitor of ELA2A could also strongly participate to elevated elastolytic activity released by IBD biopsy.

We tried to display stimuli, which could induce ELA2A up-regulation in intestinal epithelial cells. LPS represents a potential stimulus, which could trigger ELA2A over-expression. In silico analysis of CELA2A promoter (4 kb upstream to the ATG codon) revealed the presence of several TPA-responsive elements (TREs), also known as activator protein-1 (AP-1) fixation sites. AP-1 activity is regulated in a given cell by a broad range of physiological and pathological stimuli, including cytokines, growth factors, stress signals and infections. Nucleotide analysis of the CELA2A promoter region disclosed also the presence of seven putative positive glucocorticoid response elements (GREs) with the consensus GRE sequence. Glucocorticoid hormones are considered powerful immunosuppressants at pharmacological doses, but at physiological concentrations, glucocorticoids stimulate humoral and cellular immune responses (23). Stress (emotional arousal) induces an increase in endogenous glucocorticoids concentration (24). Therefore, the initial ELA2A up-regulation could be triggered by stress, which also disrupts intestinal mucus barrier favouring the contact between bacteria and colonic epithelial cells (25). The lack of ELA2A expression in germfree mice also revealed that ELA2A expression depends on a bacterial component. This suggests that ELA2A could be involved in the development of an efficient and sustainable immune system.

To study the consequences of ELA2A overexpression, we developed transgenic epithelial cells. We showed that ELA2A hyperactivity triggers degradation of junctional proteins CLAUDIN-1, OCCLUDIN and ZO-1 as well as F-actin rearrangement. This mechanism increases paracellular permeability to macromolecules and highlights the critical role of epithelial derived proteases in the increased permeability of the intestine.

The observed reduction of tight junction's proteins from ELA2A transgenic Caco-2 was not the consequence of displacement of protein into the cytoplasm. Neither was it the consequence of a reduced gene expression. Our data suggest that these proteins are degraded at the membrane level. In addition, we showed that increased ELA2A amount in the extracellular medium leads to degradation of protein components of tight junction revealing that secretory ELA2A targets these proteins. Sequence analysis of extracellular loops of OCCLUDIN highlights the presence of numerous Tyr residues but more precisely the presence of Phe-Tyr cluster into the first extracellular loop, which corresponds to preferential substrate of ELA2A.

Extracellular ELA2A activity seems to be restricted to tight junction since no abnormality was observed on the expression of VINCULLIN or E-cadherin (data not shown), which both are involved in adherens junction. Defective tight junctions were observed in non inflammatory area of intestinal mucosal tissue obtained from patients with IBD (18). Hence, tight junction leakiness at colonic level may allow penetration of luminal antigens, which promotes colonic mucosal injury and inflammation, a process suspected to play a major role in the pathogenesis of both CD and UC.

In addition to an effect on intestinal barrier function, ELA2A over-expression induced also changes in chemokine/cytokine profiles in epithelial cells. This is illustrated by CXCL8 up-regulation, but also by the decreased expression of TSLP, TGFb and IL-10, the latest being particularly important in intestinal homeostasis. On the other hand, TNF expression, a cytokine implicated in TJ disassembly, remained unchanged, further supporting the hypothesis that TJ changes observed herein were induced by elastase-mediated degradation of target proteins but not by cytokine release (26, 27). From the cytokines and growth factors evaluated, we showed that only CXCL8 upregulation is a fast consequence in response to ELA2A hyperactivity in the extracellular environment of epithelial cells, whereas the reduction of other cytokines may be a consequence of sustained ELA2A hyperactivity. TSLP decrease is consistent with a report showing that TSLP was undetectable in epithelial cells from patients with Crohn's disease, suggesting that these cells could not induce anymore the 'noninflammatory' DCs (28). In addition, TSLP deficiency prevented recovery from inflammation highlighting the critical role of this pro-TH2 cytokine in intestinal restitution and healing (29). The amount of TGFb transcript was also decreased in Tg-ELA2A Caco-2 cells. This cytokine is particular important in the maturation of resident intestinal macrophages, inducing their hypo-responsiveness against bacteria in healthy conditions (30). Together, these data provide evidence that ELA2A up-regulation modulates the mucosal immune status.

In vivo, we showed that ELA2A over-expression in colonic tissues is disadvantageous in inflammatory condition. Due to the need to use DSS to favour colonic infection by adenovirus, we were unable to highlight the role of ELA2A into tight junction opening in vivo, since in DSS condition tight junctions were already defective. The development of a genetically modified mice overexpressing ELA2A will be very helpful in the future to confirm the presented in vitro data. However, adenovirus infection was efficient to deliver CELA2A cDNA into colonic epithelial cells triggering an increase of elastolytic activity into colonic epithelial cells and consequently in the colonic lumen, suggesting that in that model, exogenous human elastase delivered by the adenovirus is secreted and active. In mice treated with DSS and injected with Ad-ELA2A, there was an increase in macrophage infiltration to the lamina propria. Although, the mediators implicated in this process remain to be elucidated, since in vitro results showed no variation of MCP1 transcriptional level in Tg-ELA2A cells (data not shown). Nonetheless, this in vivo data suggests that colonic epithelial cells, which overexpressed ELA2A trigger pathways promoting monocytes migration towards the inflammatory site.

In conclusion, we provide evidences that intestinal epithelial cells are the major source of elastolytic activity in the inflamed gut, they secrete a previously unreported form of elastase, ELA2A. In IBD conditions, correlated with a marked decrease of ELAFIN expression, ELA2A is overexpressed in epithelial cells. Our results demonstrate that hyperactive ELA2A participates to principal determinants of IBD pathogenesis: (i) increase permeability of intestinal epithelial barrier which leads to penetration of luminal products into the mucosa and (ii) induce abnormal immune status of epithelial cells leading to innate immune cells infiltration and cytokine driven inflammation.

EXAMPLE 3

As shown in FIG. 8, ELA2 over-expressing intestinal epithelial cells increase the release of CXCL8 protein compared to control cells (performed by ELISA).

The increased CXCL-8 protein release observed in ELA2A Tg cells (cells overexpressing ELA2A) is inhibited by ELAFIN addition to the culture, in a dose-dependent manner (FIG. 9).

ELA2A specific inhibition by ELAFIN is able to bring the CXCL8 protein release in ELA2ATg cells to the level of control wild-type cells.

In that case the inhibition by ELAFIN can be considered as a specific inhibition of ELA2A since:
- only ELA2A production is changed between wild type control cells and ELA2A Tg cells
- the other proteases inhibited by ELAFIN (proteinase-3 and neutrophil elastase) are not secreted or produced by intestinal epithelial cells.

REFERENCES

Throughout this application, various references describe the state of the art to which this invention pertains. The disclosures of these references are hereby incorporated by reference into the present disclosure.

1. Vergnolle N, Ferazzini M, D'Andrea M R, Buddenkotte J, and Steinhoff M. Proteinase-activated receptors: novel signals for peripheral nerves. Trends in neurosciences. 2003; 26(9):496-500.
2. Pham C T. Neutrophil serine proteases: specific regulators of inflammation. Nature reviews Immunology. 2006; 6(7):541-50.
3. Vergnolle N. Clinical relevance of proteinase activated receptors (pars) in the gut. Gut. 2005; 54(6):867-74.
4. Vergnolle N, Wallace J L, Bunnett N W, and Hollenberg M D. Protease-activated receptors in inflammation, neuronal signaling and pain. Trends in pharmacological sciences. 2001; 22(3): 146-52.
5. Motta J P, Bermudez-Humaran L G, Deraison C, Martin L, Rolland C, Rousset P, Boue J, Dietrich G, Chapman K, Kharrat P, et al. Food-grade bacteria expressing elafin protect against inflammation and restore colon homeostasis. Science translational medicine. 2012; 4(158): 158ra44.
6. Wilcz-Villega E M, McClean S, and O'Sullivan M A. Mast cell tryptase reduces junctional adhesion molecule-A (JAM-A) expression in intestinal epithelial cells: implications for the mechanisms of barrier dysfunction in irritable bowel syndrome. The American journal of gastroenterology. 2013; 108(7):1140-51.
7. Pham C T. Neutrophil serine proteases fine-tune the inflammatory response. The international journal of biochemistry & cell biology. 2008; 40(6-7):1317-33.
8. Motta J P, Magne L, Descamps D, Rolland C, Squarzoni-Dale C, Rousset P, Martin L, Cenac N, Balloy V, Huerre M, et al. Modifying the protease, antiprotease pattern by elafin overexpression protects mice from colitis. Gastroenterology. 2011; 140(4):1272-82.
9. Molodecky N A, Soon I S, Rabi D M, Ghali W A, Ferris M, Chernoff G, Benchimol E I, Panaccione R, Ghosh S, Barkema H W, et al. Increasing incidence and prevalence of the inflammatory bowel diseases with time, based on systematic review. Gastroenterology. 2012; 142(1):46-54 e42; quiz e30.
10. Van Limbergen J, Radford-Smith G, and Satsangi J. Advances in IBD genetics. Nature reviews Gastroenterology & hepatology. 2014; 11(6):372-85.
11. Gecse K, Roka R, Ferrier L, Leveque M, Eutamene H, Cartier C, Ait-Belgnaoui A, Rosztoczy A, Izbeki F, Fioramonti J, et al. Increased faecal serine protease activity in diarrhoeic IBS patients: a colonic lumenal factor impairing colonic permeability and sensitivity. Gut. 2008; 57(5): 591-9.
12. Bustos D, Negri G, De Paula J A, Di Carlo M, Yapur V, Facente A, and De Paula A. Colonic proteinases: increased activity in patients with ulcerative colitis. Medicina. 1998; 58(3):262-4.
13. Bonnart C, Deraison C, Lacroix M, Uchida Y, Besson C, Robin A, Briot A, Gonthier M, Lamant L, Dubus P, et al. Elastase 2 is expressed in human and mouse epidermis and impairs skin barrier function in Netherton syndrome through filaggrin and lipid misprocessing. The Journal of clinical investigation. 2010; 120(3):871-82.
14. Coskun M. Intestinal epithelium in inflammatory bowel disease. Frontiers in medicine. 2014; 1(24.
15. Peterson L W, and Artis D. Intestinal epithelial cells: regulators of barrier function and immune homeostasis. Nature reviews Immunology. 2014; 14(3):141-53.
16. Atreya R, and Neurath M F. IBD pathogenesis in 2014: Molecular pathways controlling barrier function in IBD. Nature reviews Gastroenterology & hepatology. 2015; 12(2):67-8.
17. Zeissig S, Burgel N, Gunzel D, Richter J, Mankertz J, Wahnschaffe U, Kroesen A J, Zeitz M, Fromm M, and Schulzke J D. Changes in expression and distribution of claudin 2, 5 and 8 lead to discontinuous tight junctions and barrier dysfunction in active Crohn's disease. Gut. 2007; 56(1):61-72.
18. Kucharzik T, Walsh S V, Chen J, Parkos C A, and Nusrat A. Neutrophil transmigration in inflammatory bowel disease is associated with differential expression of epithelial intercellular junction proteins. The American journal of pathology. 2001; 159(6):2001-9.
19. Kiesslich R, Goetz M, Angus E M, Hu Q, Guan Y, Potten C, Allen T, Neurath M F, Shroyer N F, Montrose M H, et al. Identification of epithelial gaps in human small and large intestine by confocal endomicroscopy. Gastroenterology. 2007; 133(6):1769-78.
20. Lim L G, Neumann J, Hansen T, Goetz M, Hoffman A, Neurath M F, Galle P R, Chan Y H, Kiesslich R, and Watson A J. Confocal endomicroscopy identifies loss of local barrier function in the duodenum of patients with Crohn's disease and ulcerative colitis. Inflammatory bowel diseases. 2014; 20(5):892-900.
21. Del Mar E G, Largman C, Brodrick J W, Fassett M, and Geokas M C. Substrate specificity of human pancreatic elastase 2. Biochemistry. 1980; 19(3):468-72.
22. Cleynen I, Juni P, Bekkering G E, Nuesch E, Mendes C T, Schmied S, Wyder S, Kellen E, Villiger P M, Rutgeerts P, et al. Genetic evidence supporting the association of 23. Tait A S, Butts C L, and Sternberg E M. The role of glucocorticoids and progestins in inflammatory, autoimmune, and infectious disease. Journal of leukocyte biology. 2008; 84(4):924-31.
24. Lupien S J, Maheu F, Tu M, Fiocco A, and Schramek T E. The effects of stress and stress hormones on human cognition: Implications for the field of brain and cognition. Brain and cognition. 2007; 65(3):209-37.
25. Da Silva S, Robbe-Masselot C, Ait-Belgnaoui A, Mancuso A, Mercade-Loubiere M, Salvador-Cartier C, Gillet M, Ferrier L, Loubiere P, Dague E, et al. Stress disrupts intestinal mucus barrier in rats via mucin O-glycosylation shift: prevention by a probiotic treatment. American journal of physiology Gastrointestinal and liver physiology. 2014; 307(4):G420-9.
26. Clayburgh D R, Barrett T A, Tang Y, Meddings J B, Van Eldik L J, Watterson D M, Clarke L L, Mrsny R J, and Turner J R. Epithelial myosin light chain kinase-dependent barrier dysfunction mediates T cell activation-induced diarrhea in vivo. The Journal of clinical investigation. 2005; 115(10):2702-15.
27. Marchiando A M, Shen L, Graham W V, Weber C R, Schwarz B T, Austin J R, 2nd, Raleigh D R, Guan Y, Watson A J, Montrose M H, et al. Caveolin-1-dependent occludin endocytosis is required for TNF-induced tight junction regulation in vivo. The Journal of cell biology. 2010; 189(1):111-26.
28. Rimoldi M, Chieppa M, Salucci V, Avogadri F, Sonzogni A, Sampietro G M, Nespoli A, Viale G, Allavena P, and Rescigno M. Intestinal immune homeostasis is regulated by the crosstalk between epithelial cells and dendritic cells. Nature immunology. 2005; 6(5):507-14.
29. Reardon C, Lechmann M, Brustle A, Gareau M G, Shuman N, Philpott D, Ziegler S F, and Mak T W. Thymic stromal lymphopoetin-induced expression of the endogenous inhibitory enzyme SLPI mediates recovery from colonic inflammation. Immunity. 2011; 35(2):223-35.
30. Maheshwari A, Kelly D R, Nicola T, Ambalavanan N, Jain S K, Murphy-Ullrich J, Athar M, Shimamura M, Bhandari V, Aprahamian C, et al. TGF-beta2 suppresses macrophage cytokine production and mucosal inflammatory responses in the developing intestine. Gastroenterology. 2011; 140(1):242-53.
31. Jacob C, Yang P C, Darmoul D, Amadesi S, Saito T, Cottrell G S, Coelho A M, Singh P, Grady E F, Perdue M, et al. Mast cell tryptase controls paracellular permeability of the intestine. Role of protease-activated receptor 2 and beta-arrestins. The Journal of biological chemistry. 2005; 280(36):31936-48.
32. Anderson R D, Haskell R E, Xia H, Roessler B J, and Davidson B L. A simple method for the rapid generation of recombinant adenovirus vectors. Gene therapy. 2000; 7(12):1034-8.

The invention claimed is:

1. A method for screening a candidate compound for activity as an elastase 2A (ELA2A) inhibitor or ELA2A antagonist for use in the treatment or prevention of inflammatory bowel diseases (IBD), irritable bowel syndrome (IBS) or gluten hypersensitivity, comprising
   (i) providing a purified ELA2A protein or a cell, tissue sample or organism expressing the ELA2A protein,
   (ii) providing the candidate compound,
   (iii) contacting the purified ELA2A protein or the cell, tissue sample or organism expressing the ELA2A protein with the candidate compound,
   (iv) measuring the activity of the purified ELA2A protein or ELA2A protein expressed by the cell, tissue sample or organism,
   and
   (v) selecting positively the candidate compound as an ELA2A inhibitor or ELA2A antagonist if the candidate compound blocks the action of the purified ELA2A or inhibits ELA2A expression in the cell, tissue sample or organism.

2. The method of claim 1, wherein the candidate compound is a small organic molecule, a nucleic acid, an antibody, a peptide or a polypeptide, and wherein the candidate compound is not α1-antitrypsin.

3. The method of claim 1, wherein the (iv) measuring step comprises:
   a quantitative elastolytic activity assay measuring a rate of elastin degradation, or
   a quantitative elastase inhibitor functional assay measuring a decrease in ELA2A activity.

4. A method for screening at least one candidate compound for activity as an elastase 2A (ELA2A) inhibitor or ELA2A antagonist, comprising
   (i) providing at least one cell, tissue sample or organism expressing the ELA2A protein,
   (ii) providing the at least one candidate compound,
   (iii) contacting the at least one cell, tissue sample or organism expressing the ELA2A protein with the at least one candidate compound,
   (iv) measuring the activity of the ELA2A protein expressed by the at least one cell, tissue sample or organism, and
   (v) selecting positively the at least one candidate compound as an ELA2A inhibitor or ELA2A antagonist if the at least one candidate compound inhibits ELA2A activity or expression in the at least one cell, tissue sample or organism.

5. The method of claim 4, wherein the (iv) measuring step comprises:
   a quantitative elastolytic activity assay measuring a rate of elastin degradation, or a quantitative elastase inhibitor functional assay measuring a decrease in ELA2A activity.

6. The method of claim 4, wherein the candidate compound is in a library of compounds that are screened, wherein the library of compounds is selected from the group consisting of compounds previously synthesized, compounds for which the structure is determined in a database, compounds that have been synthesized de novo and natural compounds.

7. A method for screening a library of candidate compounds for activity as an elastase 2A (ELA2A) inhibitor or ELA2A antagonist, comprising
   (i) providing a purified ELA2A protein or at least one cell, tissue sample or organism expressing the ELA2A protein,
   (ii) providing the library of candidate compounds,
   (iii) contacting purified ELA2A protein or the at least one cell, tissue sample or organism expressing the ELA2A protein with candidate compounds of the library of compounds,
   (iv) measuring the activity of the purified ELA2A protein or the ELA2A protein expressed by the at least one cell, tissue sample or organism at a suitable time after the contacting step in a quantitative elastolytic activity assay measuring a rate of elastin degradation, or a quantitative elastase inhibitor functional assay measuring a decrease in ELA2A activity, and
   (v) selecting positively any one of the candidate compounds as an ELA2A inhibitor or ELA2A antagonist if any one of the candidate compound inhibits ELA2A activity or expression in the at least one cell, tissue sample or organism, wherein the selected compound is suitable for treating a subject suffering from IBD, IBS or gluten hypersensitivity.

8. The method of claim 7, wherein the at least one candidate compound selected is an organic molecule, a nucleic acid, an antibody, a peptide or a polypeptide and is not α1-antitrypsin.

* * * * *